(12) United States Patent
Lauer

(10) Patent No.: US 6,436,085 B1
(45) Date of Patent: Aug. 20, 2002

(54) SUCTION CATHETER SYSTEM

(76) Inventor: Mark A. Lauer, 1693 Juno Ave., St. Paul, MN (US) 55116

( * ) Notice: Subject to any disclaimer, the term of this patent is extended or adjusted under 35 U.S.C. 154(b) by 152 days.

(21) Appl. No.: 09/632,123

(22) Filed: Aug. 3, 2000

(51) Int. Cl.[7] .............................................. A61M 31/00
(52) U.S. Cl. ..................................... 604/506; 604/408
(58) Field of Search ................................ 604/408, 506, 604/28; 128/200.26, 207.14, 912

(56) References Cited

U.S. PATENT DOCUMENTS

| 4,928,830 A | * | 5/1990 | Brewer ........................ 206/570 |
|---|---|---|---|
| 5,269,756 A | * | 12/1993 | Dryden ........................ 604/54 |
| 5,449,348 A | * | 9/1995 | Dryden ........................ 604/171 |
| 5,507,279 A | * | 4/1996 | Fortune et al. ........ 128/200.26 |
| 5,871,692 A | * | 2/1999 | Haire et al. .................... 422/28 |
| 6,196,963 B1 | * | 3/2001 | Williams ........................ 600/3 |

* cited by examiner

Primary Examiner—Denise L. Esquivel
Assistant Examiner—Marc Norman
(74) Attorney, Agent, or Firm—Hugh D. Jaeger

(57) ABSTRACT

A suction catheter system including a durable transparent pouch used to hold irrigating solution and a catheter in a contaminant-free environment between uses. The suction catheter system allows the practitioner to reuse the catheter several times for the same patient rather than using a new catheter for each suctioning when the practitioner needs use of both hands and has to lay the catheter down.

41 Claims, 24 Drawing Sheets

SUCTION CATHETER SYSTEM

CROSS REFERENCES TO CO-PENDING APPLICATIONS

None.

BACKGROUND OF THE INVENTION

1. Field of the Invention

A suction catheter system including a durable transparent pouch used to hold irrigating solution and a catheter in a contaminant-free environment between uses. The suction catheter system allows the practitioner to reuse the catheter several times for the same patient rather than using a new catheter for each suctioning when the practitioner needs use of both hands and has to lay the catheter down.

2. Description of the Prior Art

Prior art catheter kits included a catheter and a small basin having irrigating solution where the catheter is flushed after use. The catheter is often disposed of after each use to prevent contamination and, in the alternative, as long as the practitioner does not set the catheter down, the catheter can be reused. The problem with the prior art catheter kits, such as just described, arises when suctioning a patient. Suctioning often requires more than one or two quick suctions. Oftentimes the user places the catheter on the bed or over a contaminant-rich work surface between suctioning procedures to free up both hands for other procedures. Practitioners who follow the rules do not set the catheter down and, consequently, do not have the use of both hands during the suctioning process. Obviously, the use of both hands is preferred and desirable during the suctioning process. The present invention allows the practitioner to free up his hands because it includes a contaminant-free pouch which holds the catheter between uses.

SUMMARY OF THE INVENTION

The general purpose of the present invention is to provide a suction catheter system that can be used more than once on the same patient during the same or consecutive medical procedures.

According to one embodiment of the present invention, there is provided a transparent pouch, including surgical gloves, a catheter, and various adhesive strips used to secure the pouch to a work surface and also to hold the catheter in a manageable position between uses. A sealing path is provided along and about the upper region of the pouch for adhesive sealing of the interior of the pouch. The pouch also serves as a reservoir for irrigating solution used in the procedure.

One significant aspect and feature of the present invention is the freeing up of both of a practitioner's hands between suctioning events.

Another significant aspect and feature of the present invention is the ability to reuse a catheter multiple times during a medical procedure.

Another significant aspect and feature of the present invention is a means of holding the catheter system to a work surface.

A further significant aspect and feature of the present invention is a pouch with the capacity to hold irrigating solution.

An additional significant aspect and feature of the present invention is the double-stick tape which holds the catheter stem in an easily accessible location within the pouch.

Still another significant aspect and feature of the present invention is the contaminant-free environment provided in the pouch.

Yet another significant aspect and feature of the present invention is a pull tab or other means which allows the user to access the pouch without contaminating its interior.

Having thus briefly described an embodiment of the present invention and enumerated certain significant aspects and features thereof, it is the principal object of the present invention to provide a suction catheter system that can be used multiple times.

One object of the present invention is to provide a contaminant-free environment for holding a catheter between suctionings.

Another object of the present invention is to provide a means to reuse suction catheters.

A further object of the present invention is to provide a means of securing the suction catheter system to a work surface.

An additional object of the present invention is to provide easy access to the catheter subsequent to the initial suctioning.

Still another object of the present invention is to provide a contaminant-free pouch which holds irrigating solution for flushing debris from a catheter.

Further, while the suction catheter is held secure in the pouch, the practitioner can use both hands. The hand holding the suction catheter itself still needs to remain sterile. Sterility can be accomplished by using the paper wrap that the enclosed gloves are initially wrapped in. The sterile part of the wrap is held by the suction catheter hand which then is used to help disconnect the ventilator tubing or to take the tip off the irrigation container. Sterility can also be accomplished by using the inside sterile part of the sealing panel.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
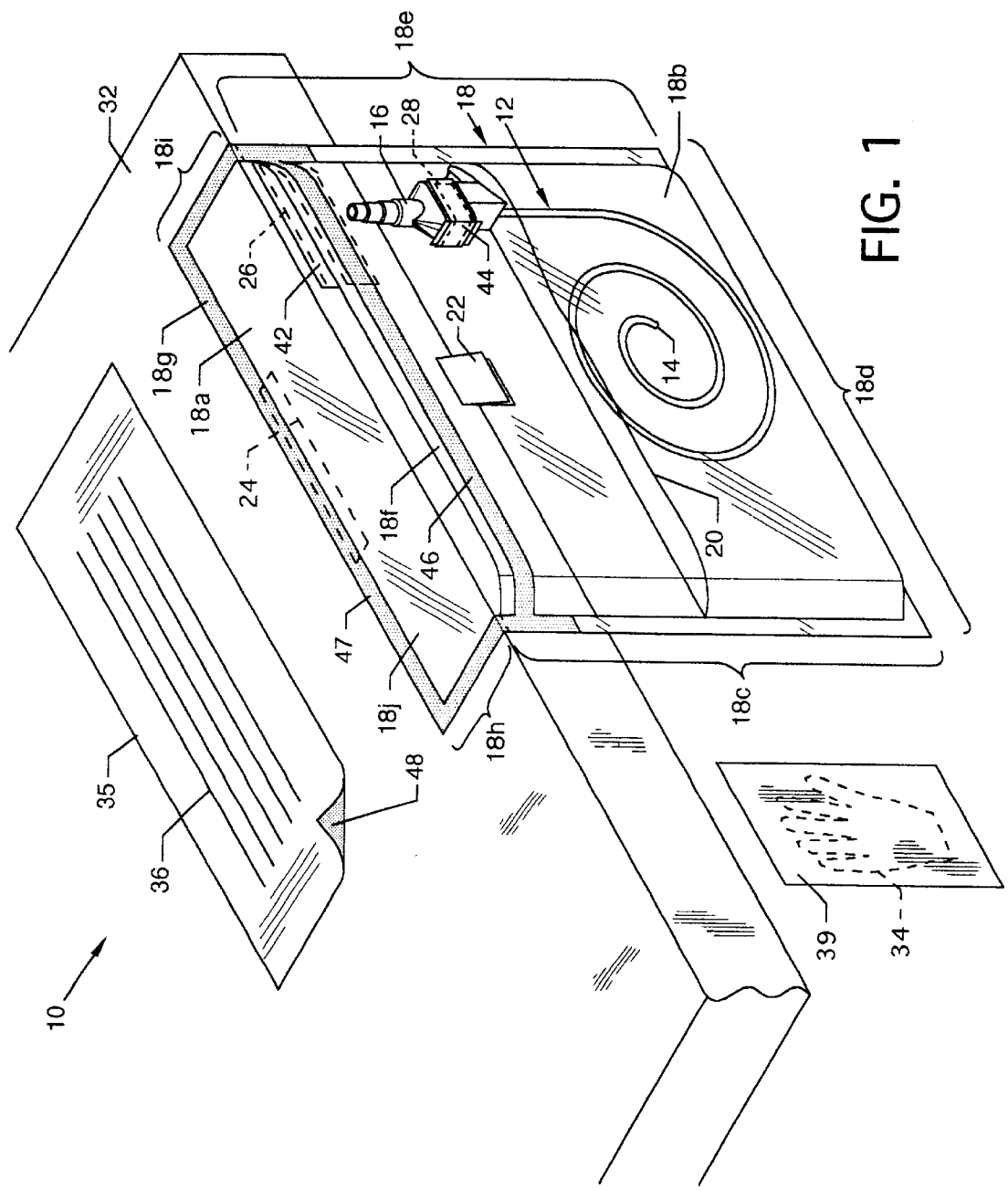
FIG. 1 illustrates an isometric view of a suction catheter system, the present invention, in a position for use.
Figure 3:
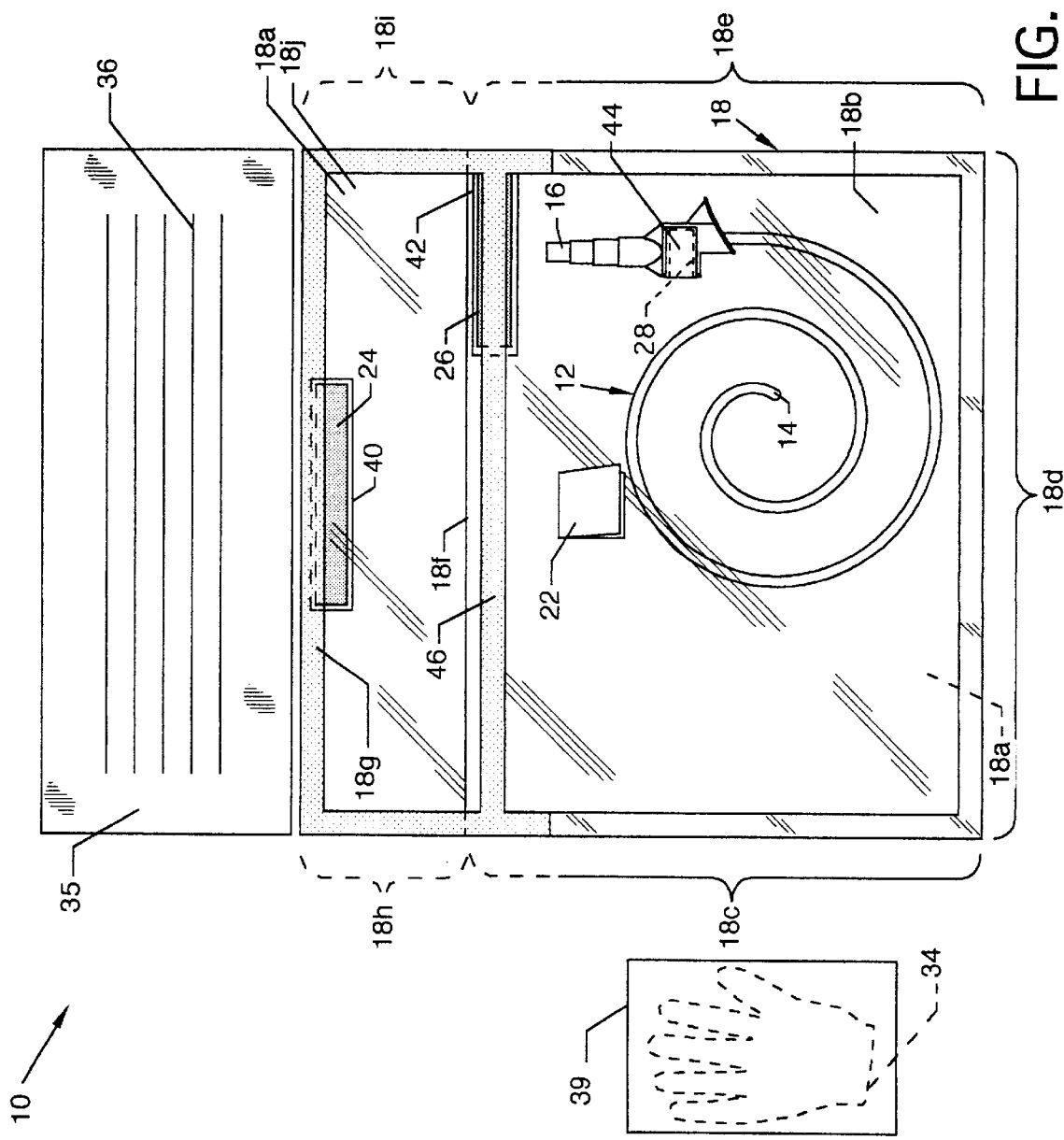
FIG. 3 illustrates a front view of the suction catheter system prior to full utilization.
Figure 4:
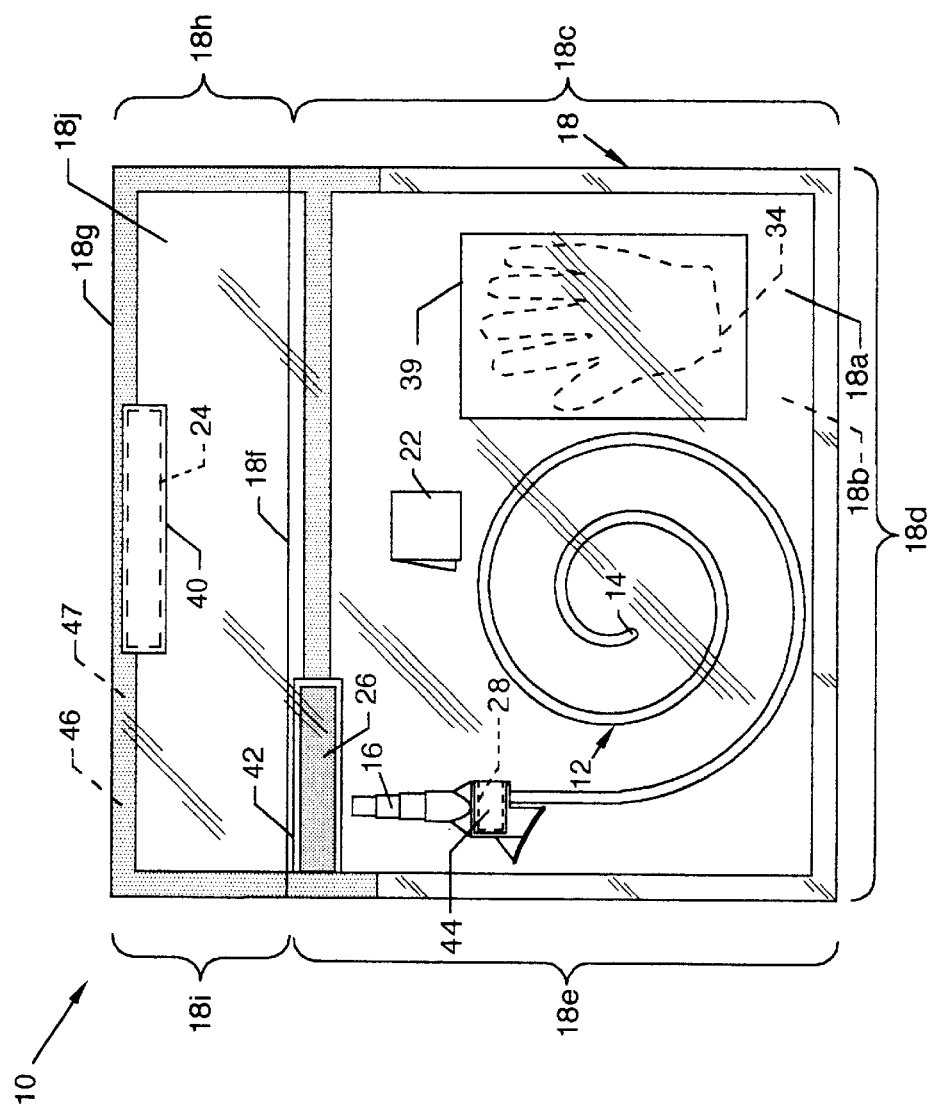
FIG. 4 illustrates a back view of the suction catheter system.

FIG. 1 illustrates an isometric view of a suction catheter system 10, the present invention, in a position for use. The suction catheter system 10 is comprised of a catheter 12 having a catheter tip 14 and a catheter stem 16, a transparent pouch 18 which holds irrigating solution 20, and other members as described herein. The transparent pouch 18, fashioned generally of durable clear and transparent flexible plastic panels, includes a rear panel 18a and a front panel 18b of shorter vertical dimension than that of the rear panel 18a. The shorter front panel 18b is suitably secured and bonded to the rear panel 18a, such as by ultrasonic welding, heat treatment, adhesive or the like, thereby forming planar connected layered planar edges including a left planar edge 18c, a bottom planar edge 18d, and a right planar edge 18e. The upper portion of the rear panel 18a forms an anchoring flap 18j. Suitably located one-time use medium pressure sensitive adhesive 48 is provided on the rear surface of a sealing panel 35 to enable sealing of the pouch 18 by the sealing panel 35. With reference to FIGS. 3 and 1, the one-time use medium pressure sensitive adhesive 48 on the rear surface of the sealing panel 35 seals along a sealing path 47 extending along the top planar edge 18g of the rear panel 18a, then from the top planar edge 18g of the rear panel 18a and along the non-layered left and right planar edges 18h and 18i, respectively, of the rear panel 18a and thence beyond the upper edge or lip 18f of the front panel 18b continuing a short distance onto the left planar edge 18c and right planar edge 18e, and horizontally across the front panel 18b between the left planar edge 18c and the right planar edge 18e in close proximity to the upper edge or lip 18f of the front panel 18b. Heat or other methods may be used to transfer the one-time use medium pressure sensitive adhesive 48 from the sealing panel 35 to the sealing path 47. In the alternative, one-time use medium pressure sensitive adhesive, shown alternatively with reference numeral 46, could be applied to the sealing path 47 in lieu of the one-time use medium pressure sensitive adhesive 48 on the rear surface of the sealing panel 35. Such adhesive arrangements offer a suitable arrangement for sealing of the pouch 18 by the sealing panel 35. As yet another alternative, suitable adhesive could be utilized to include adhesive coverage on both the rear surface of the sealing panel 35 and on the front of the pouch 18 in the planar areas previously described which utilized the one-time use medium pressure sensitive adhesive 46. In addition, instructions 36 are included on the front surface of the sealing panel 35. Also included in the invention are surgical gloves 34 in a sterile wrapping 39 which are removed during use of the invention. The pouch 18 includes a pull tab 22 attached to the front panel 18b which allows the user to easily expand the pouch 18 without contaminating its contents. The pull tab 22 is formed of a strip of material which is folded so as to create a front portion and a rear portion. The rear portion is bonded to the front panel 18b of the pouch 18. The suction catheter system 10 includes one or more double-sided adhesive strips 24 on the upper backside of the rear panel 18a of pouch 18 which secures the suction catheter system 10 in an upright fashion to a work surface 32. The work surface 32 is illustrated as an ordinary table, but the suction catheter system 10 may be secured to a patient care table, a bed rail, the top side of a cabinet, an operating room table or any other suitable structure at any suitable location. The forward side of the adhesive strip 24 adheres to the upper rearward side of the rear panel 18a by high pressure sensitive adhesive (not illustrated) and the rearward side of the adhesive strip 24 is coated with a medium pressure sensitive adhesive (not illustrated) for releasable adhesion to the work surface 32. The portion of the rear panel 18a between the planar edges 18h and 18i is folded at a right angle to the pouch 18 and is secured to the work surface 32 by the adhesive strip 24. A backing strip 40 is located on the rear of the adhesive strip 24, as shown in FIGS. 3 and 4. Such positioning presents the upper edge or lip 18f of the pouch for easy and convenient access to the interior of the pouch 18 at the level of the work surface 32. There is also provided a double-sided adhesive strip 28 with a backing strip 44 on the catheter stem 16 which may be utilized to conveniently hold the catheter 12 in the pouch 18 when not in use. Alternatively, there is another double-sided adhesive strip 26 having a backing strip 42 near the right side of the opening of the pouch 18 which serves the same purpose. All of the strips of adhesive are of a medical grade, non-latex and hypoallergenic material with the exception of any exterior strips which may or may not be of medical grade hypoallergenic material. Most hospitals and nursing homes have Formica work surfaces, and the double-sided appropriately adhesived materials can easily be removed without damaging the work surface. The uses of these adhesive strips will become more clear when described in the mode of operation. It is to be understood that the size of the adhesive strips 24, 26 and 28, as well as the pouch 18, may vary due to the size of the catheter 12 needed, and that the size in no way changes the function or use of the suction catheter system 10.

Figure 2:
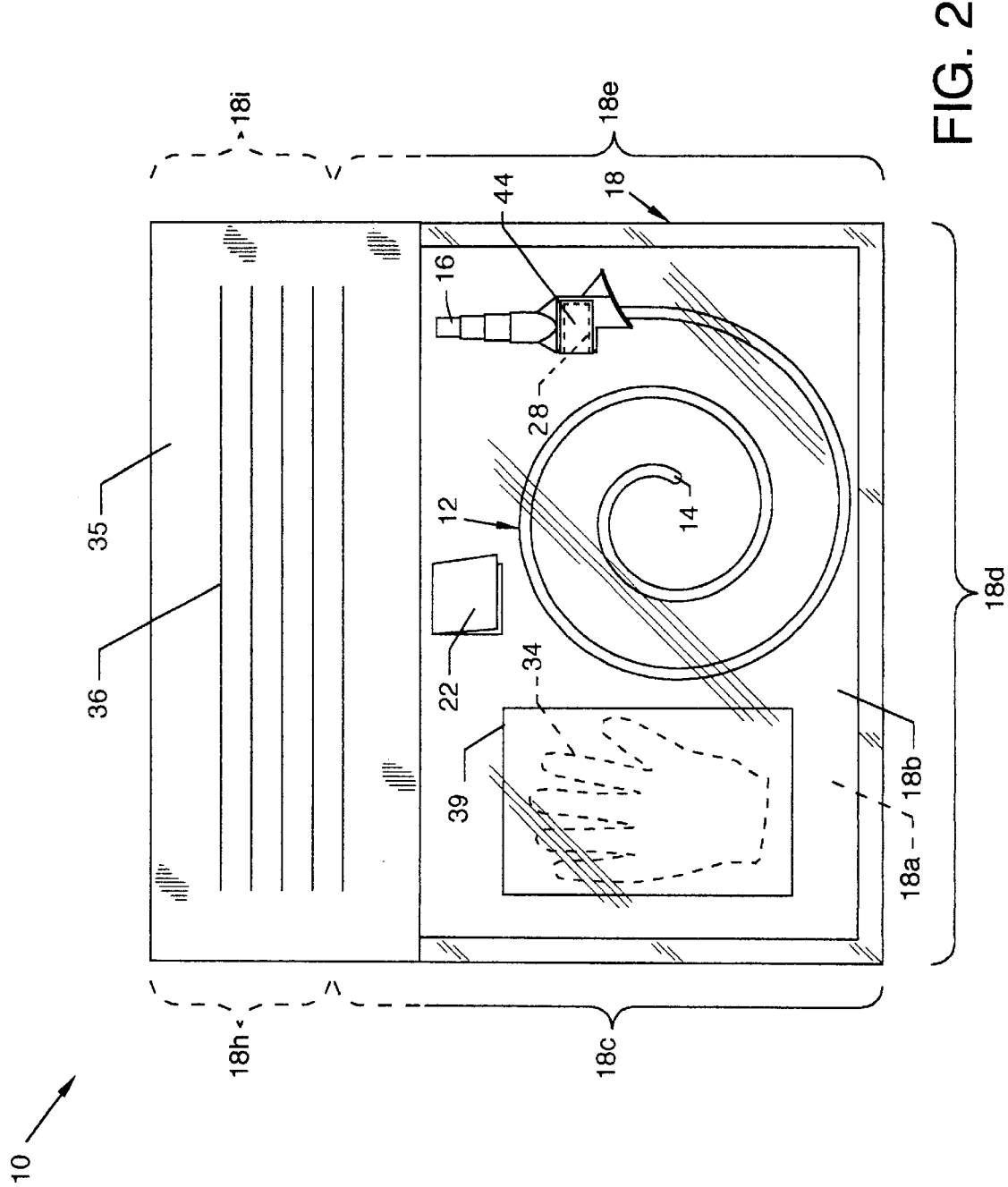
FIG. 2 illustrates a front view of the suction catheter system as it would be packaged before use.

FIG. 2 illustrates a front view of the suction catheter system 10, where all numerals correspond to those elements previously described. This illustration shows the suction catheter system 10 as it would be packaged before use, including the pouch 18, the catheter 12 contained interior to the pouch 18, an internally located and preferably packaged pair of sterile surgical gloves 34 surrounded by a sterile wrapping 39, and instructions 36 on the sealing panel 35 of pouch 18. The one-time use medium pressure sensitive adhesive 48 of the sealing panel 35 adheres to and seals off the pouch 18 and keeps it sterile until use. The surgical gloves 34 need not be included in the pouch 18 or may be discarded if the practitioner prefers another style of surgical gloves 34.

FIG. 3 illustrates a front view of the suction catheter system 10 prior to full utilization. Removal of the sealing panel 35 reveals the location of the alternatively-located one-time use medium pressure sensitive adhesive 46 and the backing strips located in the upper region of the pouch 18. The removal of the sealing panel 35 shows the location of the sealing path 47 to which the sealing panel 35 previously and sealingly adhered, which is co-located with the alternatively-placed one-time use medium pressure sensitive adhesive 46. The location of the double-sided adhesive strip 24 and backing strip 40 along the rearward side of the rear panel 18a and in close adjacent proximity to the top planar edge 18g of the rear panel 18a is shown; and the location of the doubled-sided adhesive strip 26 and backing strip 42 located between upper region and rearward side of the front panel 18b and the forward side of the rear panel 18a is shown.

FIG. 4 illustrates a back view of the suction catheter system 10, where all numerals correspond to those elements previously described. This illustration shows the suction catheter system 10 as it would be packaged before use. Illustrated in particular are the backing strips 40, 42 and 44 which protect the double-sided adhesive strips 24, 26 and 28 when packaged. The suction catheter system 10 will be more easily understood when described in the mode of operation.

With reference to FIGS. 1–3, the mode of operation is now described. First, the instructions 36 on the sealing panel 35 may be read prior to use to refresh the user's memory on the procedure for using the suction catheter system 10. Next, the sealing panel 35 is removed, thereby opening the pouch 18. The catheter 12 is gripped through the pouch 18 and the packaged surgical gloves 34 are shaken out of the pouch 18 and onto a preferably clean work surface 32. Backing strip 40 is then removed and the sealing panel 35 can be adheringly relocated to the horizontal work surface 32, if desired. The pull tab 22 is then grasped and urged in a forward direction, thus opening pouch 18 by distancing the upper edge or lip 18f of the front panel 18b, as well as the front panel 18b itself, from the rear panel 18a. Irrigating solution 20 is then poured into the pouch 18. The suction catheter system 10 may be used without irrigating solution if it is not required for the suctioning procedure. The practitioner then dons the surgical gloves 34 and removes the backing strip 42 inside pouch 18 or the backing strip 44 on the catheter stem 16. When ready to use, the practitioner removes the catheter 12 from pouch 18 and appropriately connects it to the suctioning apparatus. The patient can now be suctioned. Once the initial suctioning is completed, the catheter tip 14 may be inserted into the irrigating solution 20 where the suctioning apparatus flushes debris out of the catheter 12, preparing it for its next use. The catheter 12 is then coiled up and placed back in the irrigating solution 20 where the catheter stem 16 is temporarily secured to the inside of the pouch 18 by means of the adhesive strip 28 on the catheter stem 16 as shown in FIG. 1 or is temporarily secured to the inside of pouch 18 by adhesive strip 26. In order to secure the catheter stem 16 to the inside of pouch 18 without contaminating it, the catheter stem 16 is adheringly positioned to the appropriate adhesive surface by squeezing the outside of pouch 18 to force contact therewith. When the practitioner is ready for the next suctioning, the catheter stem 16 is easily removed from the inside walls of pouch 18 by overcoming the adhesion of the utilized adhesive strip. This procedure may be repeated as many times as necessary using the same suction catheter system. When suctioning is complete, the entire pouch 18, catheter 12 and irrigating solution 20 are thrown away. The suction catheter system 10 may be easily adapted for use with other types of catheters and other medical and dental instruments requiring a contaminant-free holding area. To prevent contamination of the catheter when the use of both hands is required, the practitioner can utilize the inner and sterile surface of the sealing panel 35.

During opening of the pouch 18, the practitioner places the sealing panel 35 on a convenient work surface with the sterile side facing up. The sealing panel, having one upwardly-facing sterile surface, acts as a barrier when the use of both hands is required for other procedures. The sealing panel 35 can be picked up easily with the sterile gloved hand that will hold the catheter tip 14. This same gloved hand can then be used to disconnect the ventilator tubing from the endotracheal tube or to remove the tip from the irrigating solution container. Another option is for the practitioner to use the sterile paper wrapping 39 that housed the surgical gloves 34 to keep the catheter hand sterile.

Figure 5:
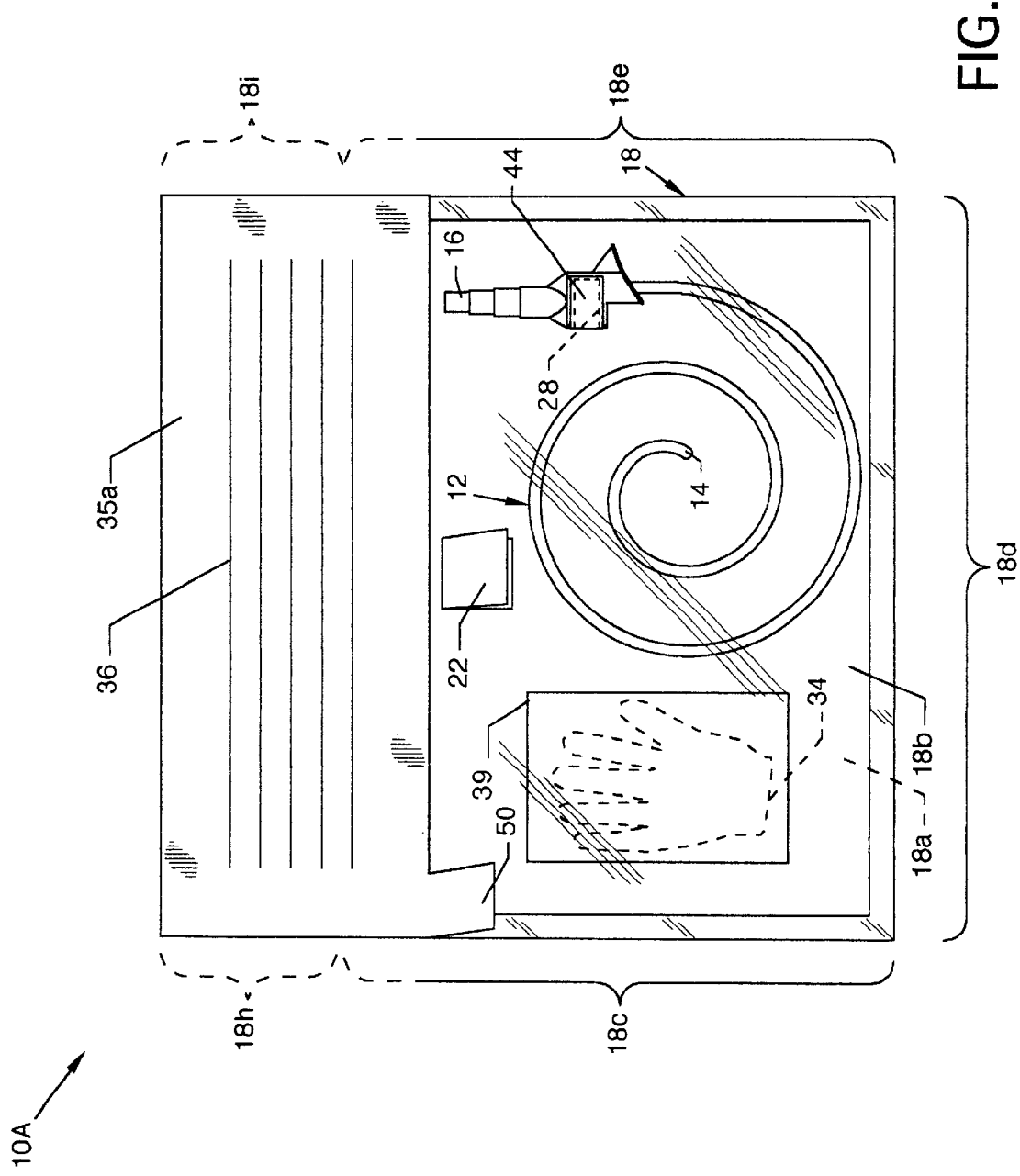
FIG. 5, a first alternative embodiment, illustrates a front view of a suction catheter system.

FIG. 5, a first alternative embodiment, illustrates a suction catheter system 10A, where all numerals previously mentioned correspond to those elements previously described, incorporating a sealing panel 35a similar in construction to the previously described sealing panel 35, but in addition having a pull tab 50 extending from the lower edge of the sealing panel 35a. The location of the one-time use medium pressure sensitive adhesive 48, as previously described, is also utilized at the rear surface of the sealing panel 35a to seal against the sealing path 47 of the pouch 18 to effect a sealed interior of the pouch 18. The rear surface of the pull tab 50 does not include the one-time use medium pressure sensitive adhesive 46 and thus the pull tab 50 can be readily grasped for removal of the panel 35a from and for quick access to the pouch 18.

Figure 6:
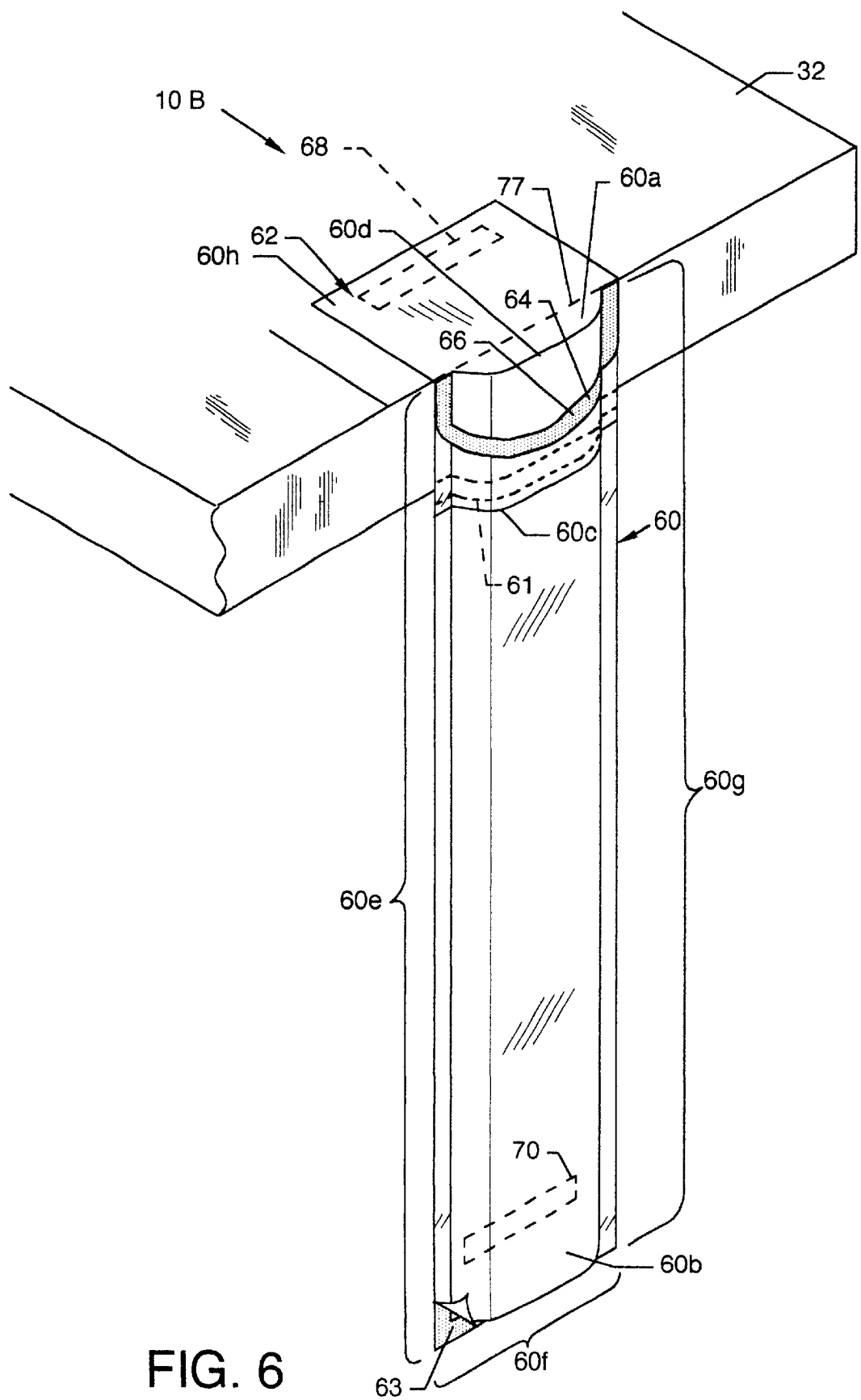
FIG. 6, a second alternative embodiment, illustrates an isometric view of a suction catheter system represented by its most prominent feature, an elongated pouch, that feature occasioning the name elongated pouch system by which this alternative embodiment is also known.
Figure 7:
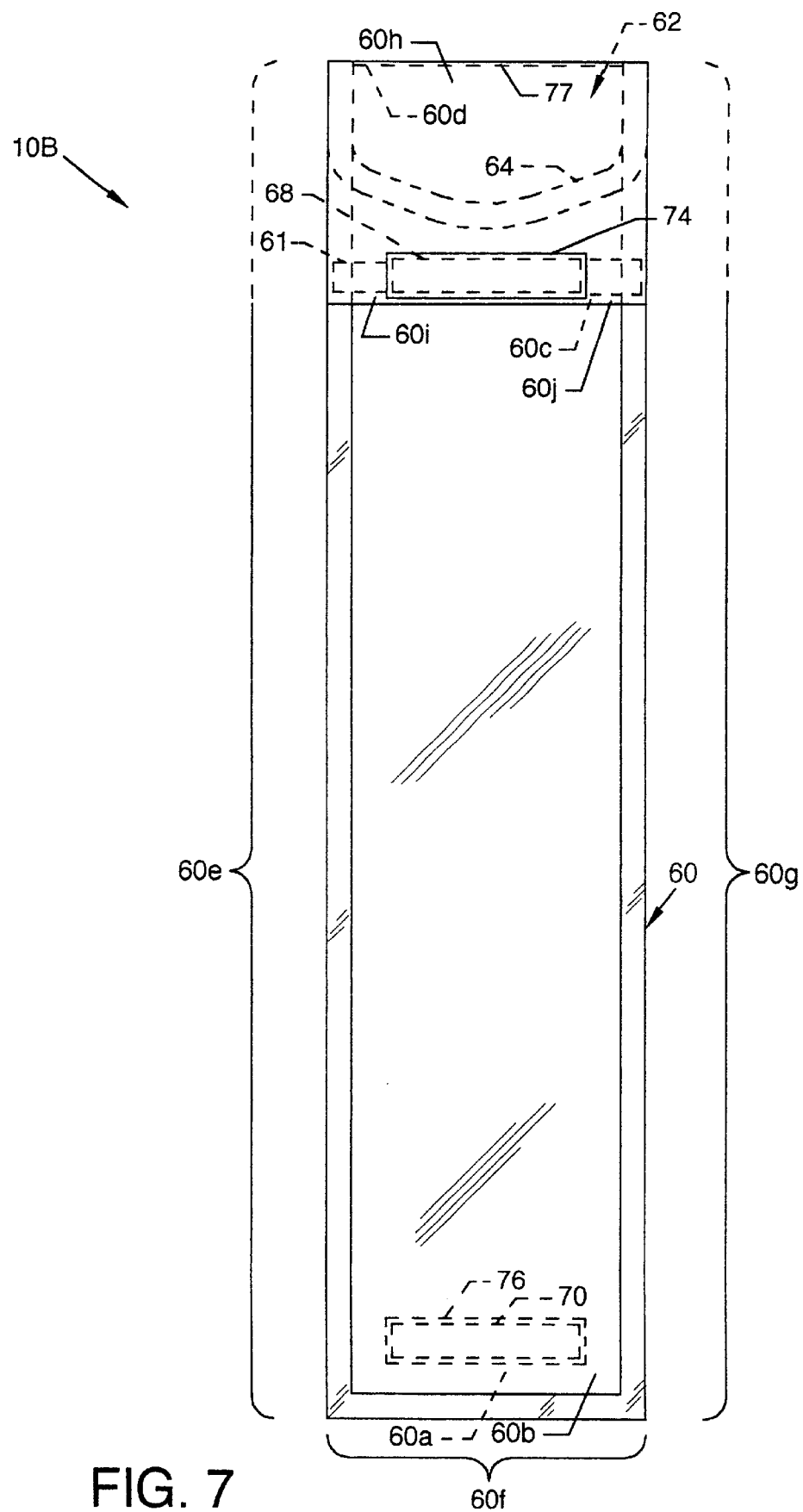
FIG. 7 illustrates a front view of the elongated pouch system, as presented for use.
Figure 8:
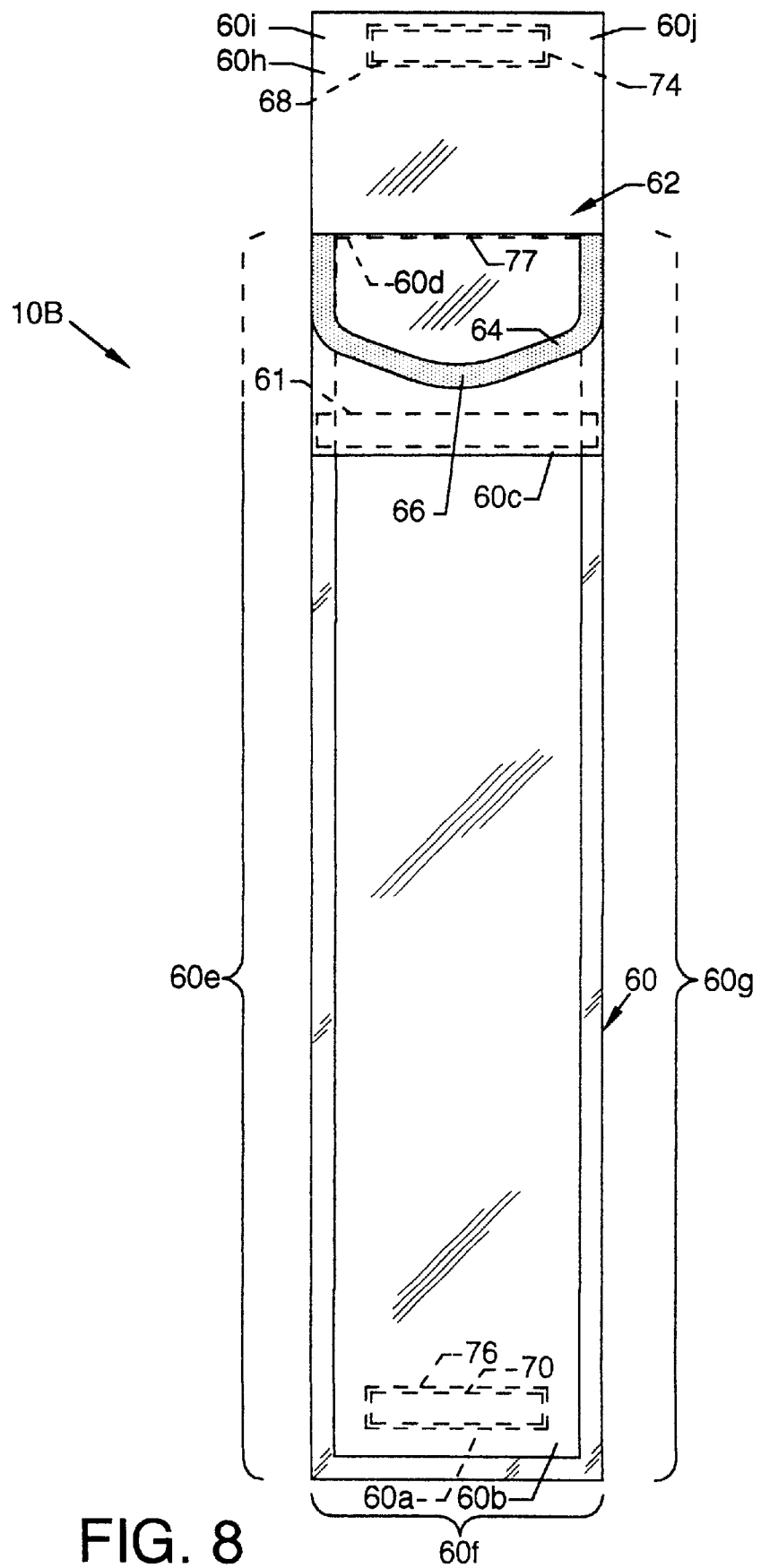
FIG. 8 illustrates a front view of the elongated pouch system of FIG. 6 prior to full utilization.

FIG. 6, a second alternative embodiment, illustrates an isometric view of a suction catheter system 10B, the present invention, in a position for use. The suction catheter system 10B is represented by its most prominent feature, an elongated pouch 60, which holds a suction tube or other medical device, not illustrated, and which is constructed in accordance with many of the elements and structures described in FIGS. 1–5. The elongated pouch 60 is fashioned of a rear panel 60a which is continuous with an anchoring flap 60h of TYVEK® or other suitable material, and a front panel 60b of durable clear and transparent flexible plastic material of shorter vertical dimension than that of the rear panel 60a. The shorter front panel 60b can include extra panel material to allow for outward expansion for carriage of a suction tube. A flap 60c, being continuous with the front panel 60b, foldingly extends in close proximity back along the upper region of the front panel 60b to form an upper edge or lip 60d at the top of the elongated pouch 60. The lower edge of flap 60c is attached or anchored to the front panel 60b by a high pressure sensitive double-sided adhesive strip 61 or a highly adhesive glue disposed therebetween. In the alternative, more than one double-sided adhesive strip may be used in lieu of a single double-sided adhesive strip 61. The shorter front panel 60b is suitably secured in a durable fashion by a high pressure sensitive adhesive 63 or, alternatively, can be bonded to the rear panel 60a, such as by ultrasonic welding, heat treatment, other types of adhesive or the like, thereby forming durable planar connected layered planar edges including a left planar edge 60e, a bottom planar edge 60f, and a right planar edge 60g. Durably sealed planar edges protect the integrity of the elongated pouch 60 should overstressing occur during opening of the elongated pouch 60 or by inadvertent tension applied by a contained suction tube when the suction tube is clumsily removed from or when sideways pressure is exerted by improper removal of the suction tube or other device from the elongated pouch 60. The anchoring flap 60h, being a part of and an extension of the rear panel 60a, is utilized in anchoring the suction catheter system 10B to a suitable work surface, as later described in detail. Also, included on the upwardly-facing surface of the anchoring flap 60h is a one-time use medium pressure sensitive adhesive 62 which is heated by a shaped contact or other suitable heater to melt and transfer the one-time use medium pressure sensitive adhesive 62 along a sealing path 64 on the forward surface of the flap 60c suitably shaped as a chevron or other suitable shape. Such transferred one-time use medium pressure sensitive adhesive 62 has a filmy quality subsequent to transfer and is then readily visible on the flap 60c. The suitably located one-time use medium pressure sensitive adhesive 62 is transferringly located on the outwardly-facing surface of the flap 60c and seals the elongated pouch 60 along and about the anchoring flap 60h. In the alternative, one-time use medium pressure sensitive adhesive, shown alternatively with reference numeral 66, could be applied to the sealing path 64 just described in lieu of the one-time use medium pressure sensitive adhesive 62 which is adheringly transferred to the flap 60c. Such adhesive arrangements offer a suitable arrangement for sealing of the elongated pouch 60 by the anchoring flap 60h. As yet another alternative, suitable adhesive could be utilized to include adhesive coverage on both the anchoring flap 60h and on the front of the flap 60c of the elongated pouch 60 to provide for adhesion along the sealing path 64. The suction catheter system 10B includes an upper double-sided adhesive strip 68 and a similarly fashioned lower double-sided adhesive strip 70 on the backside of the anchoring flap 60h and on the lower rear-facing surface of the rear panel 60a. The upper double-sided adhesive strip 68 secures the suction catheter system 10B in an upright fashion to a work surface 32. The work surface 32 is illustrated as an ordinary table, but the suction catheter system 10B may be secured to a patient care table, a bed rail, the top side of a cabinet, an operating room table or any other suitable structure at any suitable location. The lower double-sided adhesive strip 70 is used to suitably anchor the bottom of the elongated pouch 60 to a suitable surface, if present. One side of the adhesive strip 68 adheres to the rear surface of the anchoring flap 60h by high pressure sensitive adhesive (not illustrated) and the rearward side of the adhesive strip 68 is coated with a medium pressure sensitive adhesive (not illustrated) for releasable adhesion to the work surface 32. A backing strip 74 is located on the outward surface of the adhesive strip 68 and a backing strip 76 is located on the outward surface of the double-sided adhesive strip 70, as shown in FIGS. 7 and 8. All of the strips can be of adhesive of a medical grade, non-latex and hypoallergenic material, if desired. Most hospitals and nursing homes have Formica work surfaces, and the double-sided appropriately adhesive materials can easily be removed without damaging the work surface.

FIG. 7 illustrates a front view of the suction catheter system 10B, where all numerals mentioned previously correspond to those elements previously described. This illustration shows the suction catheter system 10B as it would be packaged before use, including the pouch 60. The one-time use medium pressure sensitive adhesive 62 of the anchoring flap 60h adheres to and seals off the elongated pouch 60, as previously described, and keeps it sterile until use. The chevron shape of the sealing path 64 lends to both sealing of the anchoring flap 60h to the flap 60c to provide for a sterile pouch interior and for the providing of ready access for manual grasping of and the de-adhering of the anchoring flap 60h from flap 60c when access to the interior of the elongated pouch 60 is required. The regions between the anchoring flap 60h and flap 60c lying downwardly from the chevron-shaped sealing path 64 are free floating and unsecured so that the corners 60i and 60j of the anchoring flap 60h may be readily grasped and repositioned to break the seal along the sealing path 64 in order to allow rotational repositioning of the anchoring flap 60h about line 77, as shown in FIG. 6.

FIG. 8 illustrates a front view of the suction catheter system 10B prior to full utilization. Rotation of the anchoring flap 60h about line 77 reveals the locations of the alternatively-located one-time use medium pressure sensitive adhesive 66, the backing strip 74 located on the now rearwardly-facing surface of the anchoring flap 60h, and the high pressure sensitive double-sided adhesive strip 61 securing the flap 60c to the front panel 60b. The rotation of the anchoring flap 60h also shows the location of the sealing path 64 to which the anchoring flap 60h previously and sealingly adhered, which is co-located with the alternatively-placed one-time use medium pressure sensitive adhesive 66.

Figure 9:
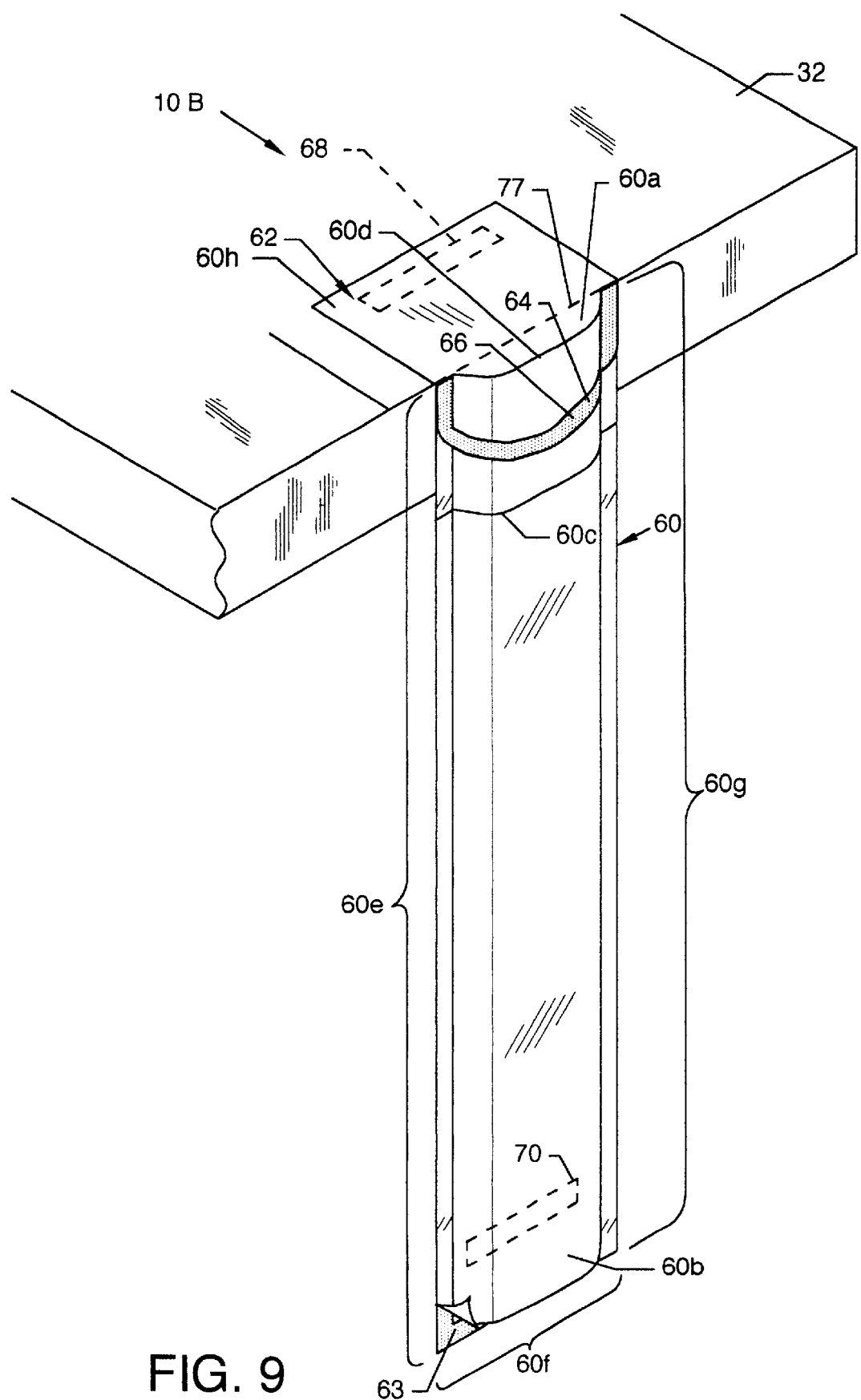
FIG. 9 illustrates the suction catheter shown in FIG. 6 but not including the high pressure sensitive double-sided adhesive strip.

FIG. 9 illustrates the suction catheter system 10B shown in FIG. 6, but not including the high pressure sensitive double-sided adhesive strip 61 which secured the flap 60c to the front panel 60b. Flap 60c is not secured to the front surface of the front panel 60b, but is merely folded along line 77 and positioned adjacent to the upper and outer region of the front panel 60b subsequent to disengagement of the flap 60c from the anchoring flap 60h to allow access between the front and rear panels 60a and 60b.

Figure 10:
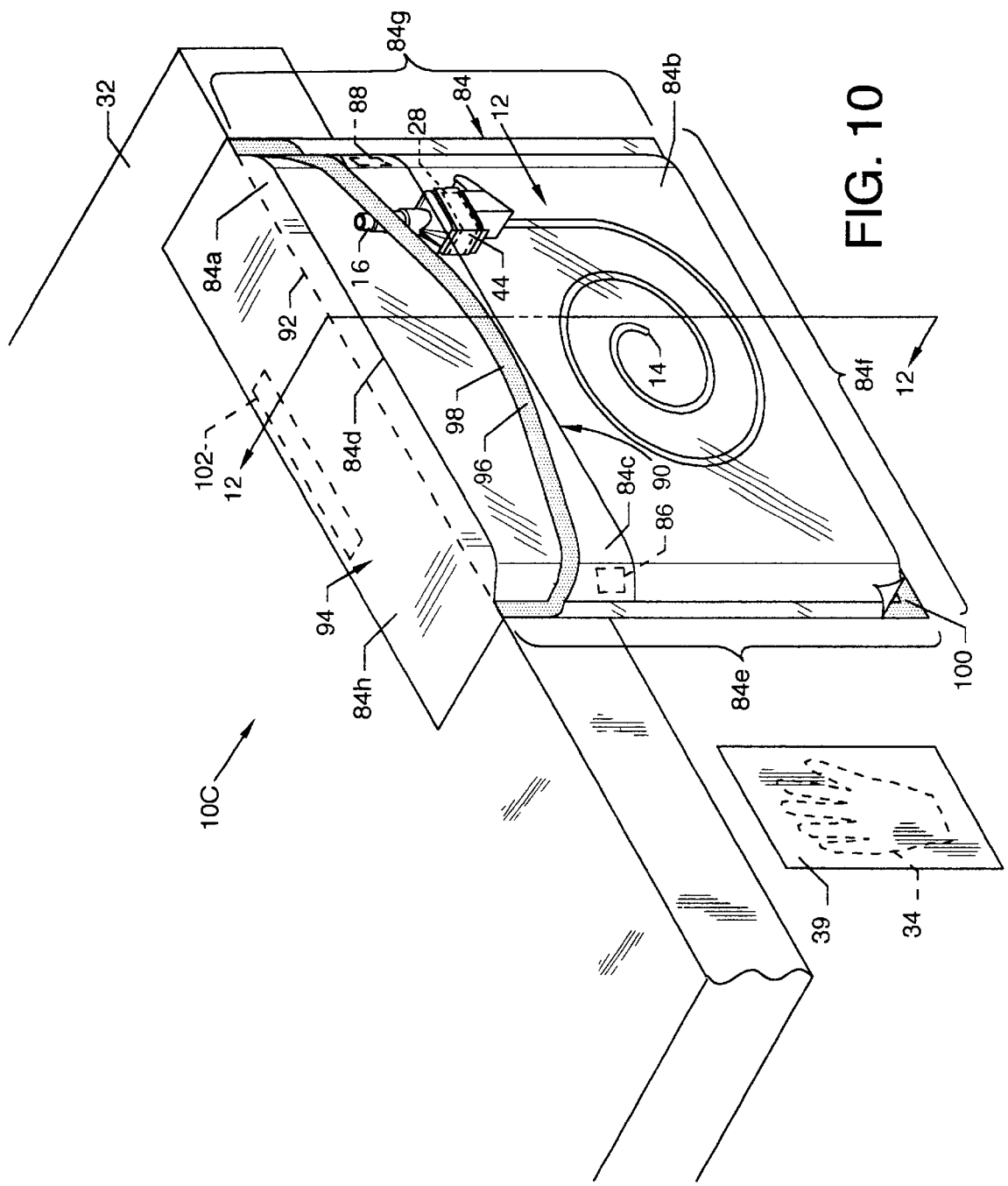
FIG. 10, a third alternative embodiment, illustrates an isometric view of a suction catheter system in a position for use.
Figure 11:
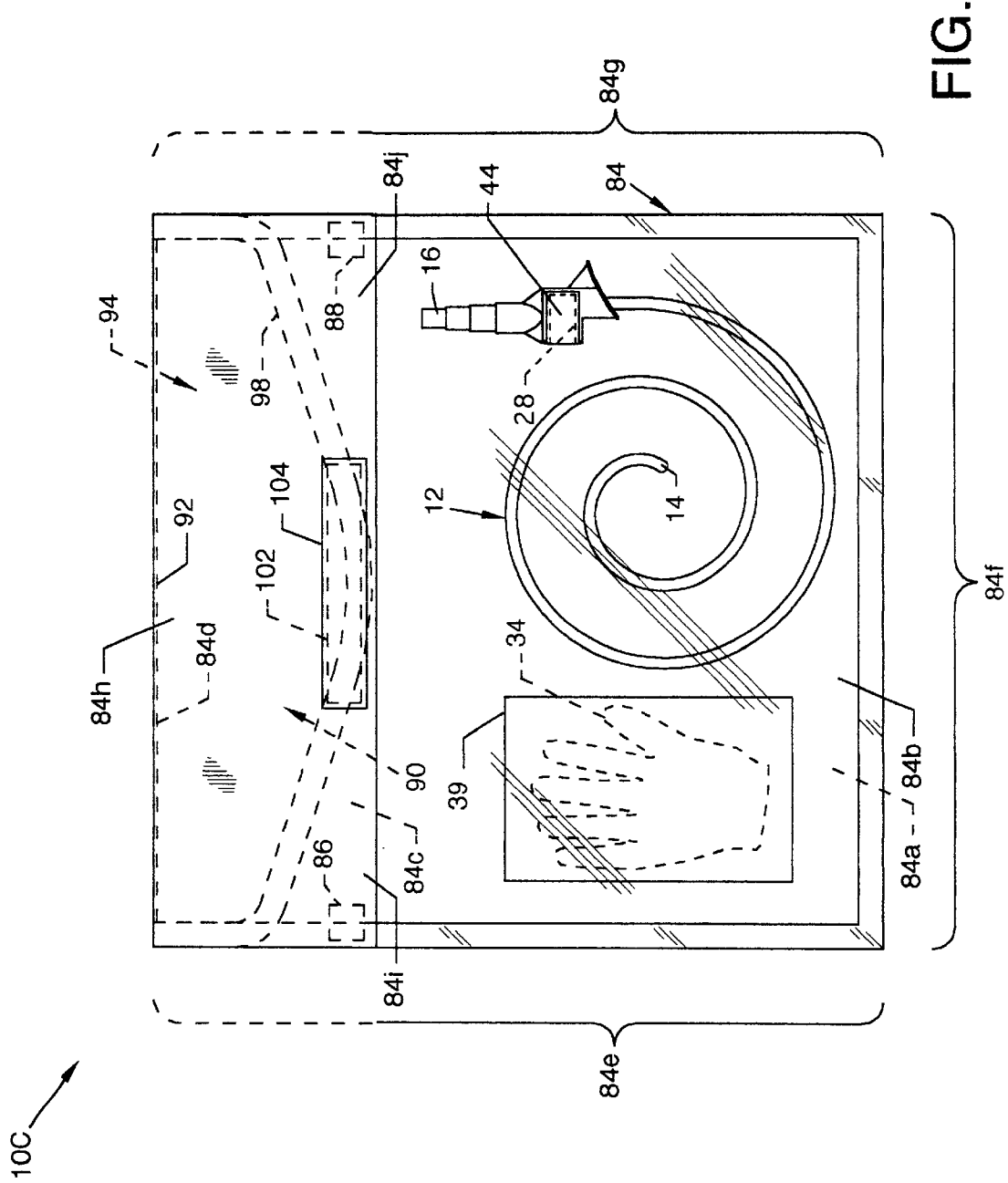
FIG. 11 illustrates a front view of the suction catheter system of FIG. 10 as it would be packaged for use.
Figure 12:
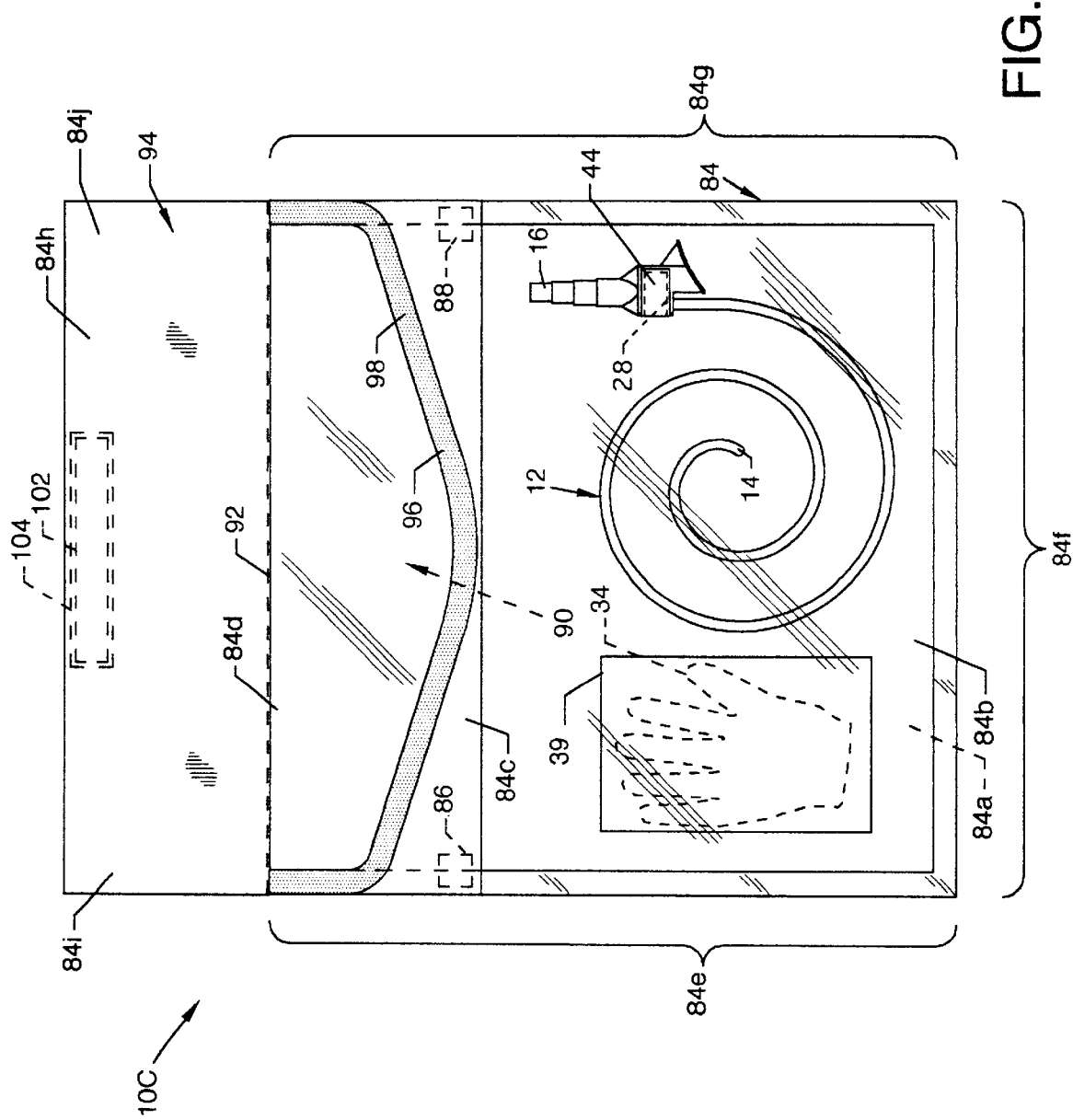
FIG. 12 illustrates a front view of the suction catheter system of FIG. 10 prior to full utilization.

FIG. 10, a third alternative embodiment, illustrates an isometric view of a suction catheter system 10C, the present invention, in a position for use. The suction catheter system 10C is comprised of a catheter 12, having a catheter tip 14 and a catheter stem 16, a transparent pouch 84 which holds irrigating solution (not illustrated), and other members as described herein. The transparent pouch 84 is fashioned of a rear panel 84a which includes an anchoring flap 84h of TYVEK® or other suitable material, and a front panel 84b of durable clear and transparent flexible plastic material of shorter vertical dimension than that of the rear panel 84a. A flap 84c, being continuous with the front panel 84b, foldingly extends in close proximity back along the front panel 84b to form an upper edge or lip 84d at the top of the pouch 84, the lower corners of which are attached or anchored to the front panel 84b by high pressure sensitive double-sided adhesive strips 86 and 88 or by a highly adhesive glue disposed therebetween. The area between the flap 84c and the front panel 84b forms a flexible compartment 90 utilized to manually deploy and outwardly expand the pouch 84 without contaminating the contents. The shorter front panel 84b is suitably secured in a durable fashion by a high pressure sensitive adhesive 100 or, alternatively, can be bonded to the rear panel 84a, such as by ultrasonic welding, heat treatment, other types of adhesive or the like, thereby forming durable planar connected layered planar edges including a left planar edge 84e, a bottom planar edge 84f, and a right planar edge 84g. Durably sealed planar edges protect the integrity of the pouch 84 should overstressing occur during opening of the pouch 84 or by inadvertent tension applied to the catheter 12 when the catheter stem 16 is secured to the pouch 84 by the double-sided adhesive strip 28. The rear panel 84a is folded along a line 92 to form the anchoring flap 84h, being part of the rear panel 84a, which is utilized in anchoring the suction catheter system 10C to a suitable work surface 32. Also, included on the upwardly-facing surface of the anchoring flap 84h is a one-time use medium pressure sensitive adhesive 94 which is clear and which is heated by a shaped contact or other suitable heater to melt and transfer the one-time use medium pressure sensitive adhesive 94 along a sealing path 98 on the forward surface of the flap 84c suitably shaped as a chevron or other suitable shape. Such transferred one-time use medium pressure sensitive adhesive 94 has a filmy quality subsequent to transfer and is then readily visible on the flap 84c. The suitably located one-time use medium pressure sensitive adhesive 94 is located on the outwardly-facing surface of the flap 84c and seals the pouch 84 along and about the anchoring flap 84h. In the alternative, one-time use medium pressure sensitive adhesive, shown alternatively with reference numeral 96, could be applied to the sealing path 98 just described in lieu of the one-time use medium pressure sensitive adhesive 94 which is adheringly transferred to the flap 84c. Such adhesive arrangements offer a suitable arrangement for sealing of the pouch 84 by the anchoring flap 84h. As yet another alternative, suitable adhesive could be utilized to include adhesive coverage on both the anchoring flap 84h and on the front of the flap 84c of the pouch 84 to provide for adhesion along the sealing path 98. Also included in the invention are surgical gloves 34 in a sterile wrapping 39 which are removed during use of the invention. The suction catheter system 10C includes one or more double-sided adhesive strips 102 on the upper backside of the anchoring flap 84h which secures the suction catheter system 10C in an upright fashion to a work surface 32. The work surface 32 is illustrated as an ordinary table, but the suction catheter system 10C may be secured to a patient care table, a bed rail, the top side of a cabinet, an operating room table or any other suitable structure at any suitable location. One side of the adhesive strip 102 adheres to the rear surface of the anchoring flap 84h by high pressure sensitive adhesive (not illustrated) and the rearward side of the adhesive strip 102 is coated with a medium pressure sensitive adhesive (not illustrated) for releasable adhesion to the work surface 32. A backing strip 104 is located on the rear of the adhesive strip 102, as shown in FIGS. 11 and 12. There is also provided a double-sided adhesive strip 28 on the catheter stem 16 which may be utilized to conveniently hold the catheter 12 in the pouch 84 when not in use. Alternatively, the catheter stem 16 can be secured to the backside of the front panel 84b at the region rearwardly adjacent to the flexible compartment 90 and/or at a location near the upper edge or lip 84d. All of the strips of adhesive can be of a medical grade, non-latex and hypoallergenic material, if desired. Most hospitals and nursing homes have Formica work surfaces, and the double-sided appropriately adhesive materials can easily be removed without damaging the work surface. The uses of these adhesive strips will become more clear when described in the mode of operation. It is to be understood that the size of the adhesive strips 102 and 28, as well as the pouch 84, may vary due to the size of the catheter 12 needed, and that the size in no way changes the function or use of the suction catheter system 10C.

FIG. 11 illustrates a front view of the suction catheter system 10C, where all numerals mentioned previously correspond to those elements previously described. This illustration shows the suction catheter system 10C as it would be packaged before use, including the pouch 84, the catheter 12 contained interior to the pouch 84, and an internally located and preferably packaged pair of sterile surgical gloves 34 surrounded by a sterile wrapping 39. The one-time use medium pressure sensitive adhesive 94 of the anchoring flap 84h adheres to and seals off the pouch 84, as previously described, and keeps it sterile until use. The chevron shape of the sealing path 98 lends to both sealing of the anchoring flap 84h to the flap 84c to provide for a sterile pouch interior and for the providing of ready access for manual grasping of and the de-adhering of the anchoring flap 84h from flap 84c when access to the interior of the pouch 84 is required. The regions between the anchoring flap 84h and flap 84c lying downwardly from the chevron-shaped sealing path 98 are free floating and unsecured so that the corners 84i and 84j may be readily grasped and repositioned to break the seal along the sealing path 98 in order to allow rotational repositioning of the anchoring flap 84h about line 92, as shown in FIG. 12. The surgical gloves 34 need not be included in the pouch 84 or may be discarded if the practitioner prefers another style of surgical gloves 34.

FIG. 12 illustrates a front view of the suction catheter system 10C prior to full utilization. Rotation of the anchoring flap 84h about line 92 reveals the locations of the alternatively-located one-time use medium pressure sensitive adhesive 96, the backing strip 104 and double-sided adhesive strip 102 located on the now rearwardly-facing surface of the anchoring flap 84h, and the high pressure sensitive double-sided adhesive strips 86 and 88 securing the flap 84c to the front panel 84b. The rotation of the anchoring flap 84h also shows the location of the sealing path 98 to which the anchoring flap 84h previously and sealingly adhered, which is co-located with the alternatively-placed one-time use medium pressure sensitive adhesive 96.

Figure 13:
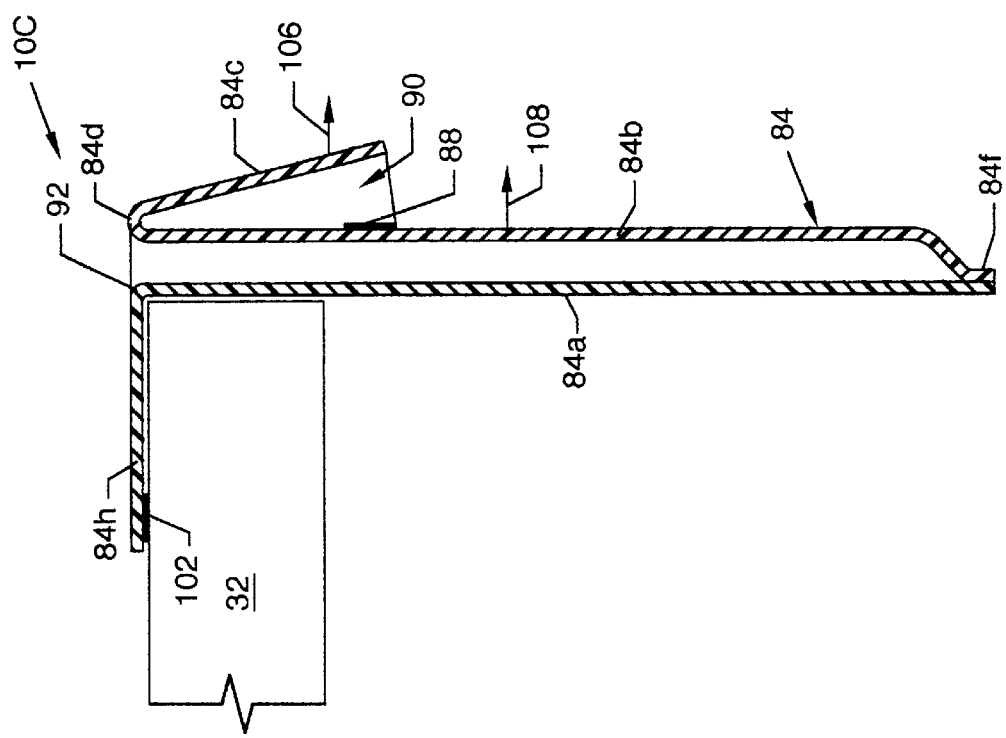
FIG. 13 illustrates a cross sectional view along line 12—12 of FIG. 10 showing activation of the pouch.

FIG. 13 illustrates a view in cross section along line 12—12 of FIG. 10 illustrating the activation and opening of the pouch 84 for the receiving of fluid by the pouch 84. The anchoring flap 84h adheres to the work surface 32 by utilizing the double-sided adhesive strip 102. opening of the interior of the pouch 84 is initiated by inserting one or more fingers into the flexible compartment 90 and exerting pressure outwardly to initiate outward movement, as shown, along arrow 106. Forces transmitted by the flap 84c are transmitted by the upper edge or lip 84d and by the high pressure sensitive double-sided adhesive strips 86 and 88 between the flap 84c and the front panel 84b to expand the front panel 84b in an outward direction, as indicated by arrow 108, to open the pouch 84.

MODE OF OPERATION

Instructional use of suction catheter system 10C:
1. Open seal along sealing path 98 on pouch 84 to the fold line 92.
2. Drop gloves 34 and sterile wrapping 39 out of pouch 84 onto working surface keeping the catheter 12 in the pouch 84.
3. Attach the pouch 84 to horizontal work surface 32 with double-sided adhesive strip 102 provided on the back of the anchoring flap 84h.
4. Fill the pouch 84 with irrigating solution, as desired, using the flexible compartment 90 to open pouch 84.

5. Don gloves 34.
6. Attach suction catheter 12 to suction tubing and suction patient. The hand holding suction tubing should only touch the vent part of the suction catheter stem 16 to keep the rest of the catheter 12 sterile.
7. Irrigate catheter 12, as needed, with solution in the pouch 84.
8. To replace catheter 12 in pouch 84, form a circle with catheter 12 and place into pouch 84. Pinch catheter stem 16 to inner front part of pouch 84 at upper edge or lip 84*d* to keep the catheter 12 in the pouch 84. Keep the vent opening part of catheter 12 up to avoid the vent opening from touching the pouch 84.
9. Now, both hands are free to use. Use the sterile paper wrap 39 which the gloves 34 come in to provide a barrier for the hand that holds the catheter 12. Preferably, the paper is doubled up to provide extra strength keeping the sterile part of the paper to the practitioner's hands. Both hands can be used to open the tracheal irrigating container or to take ventilator tubing off the tracheal tube.
10. Upon completion of the procedure, the catheter 12, gloves 34, sterile wrapping 39, and the pouch 84 may be disposed of in a suitable manner.

Figure 14:
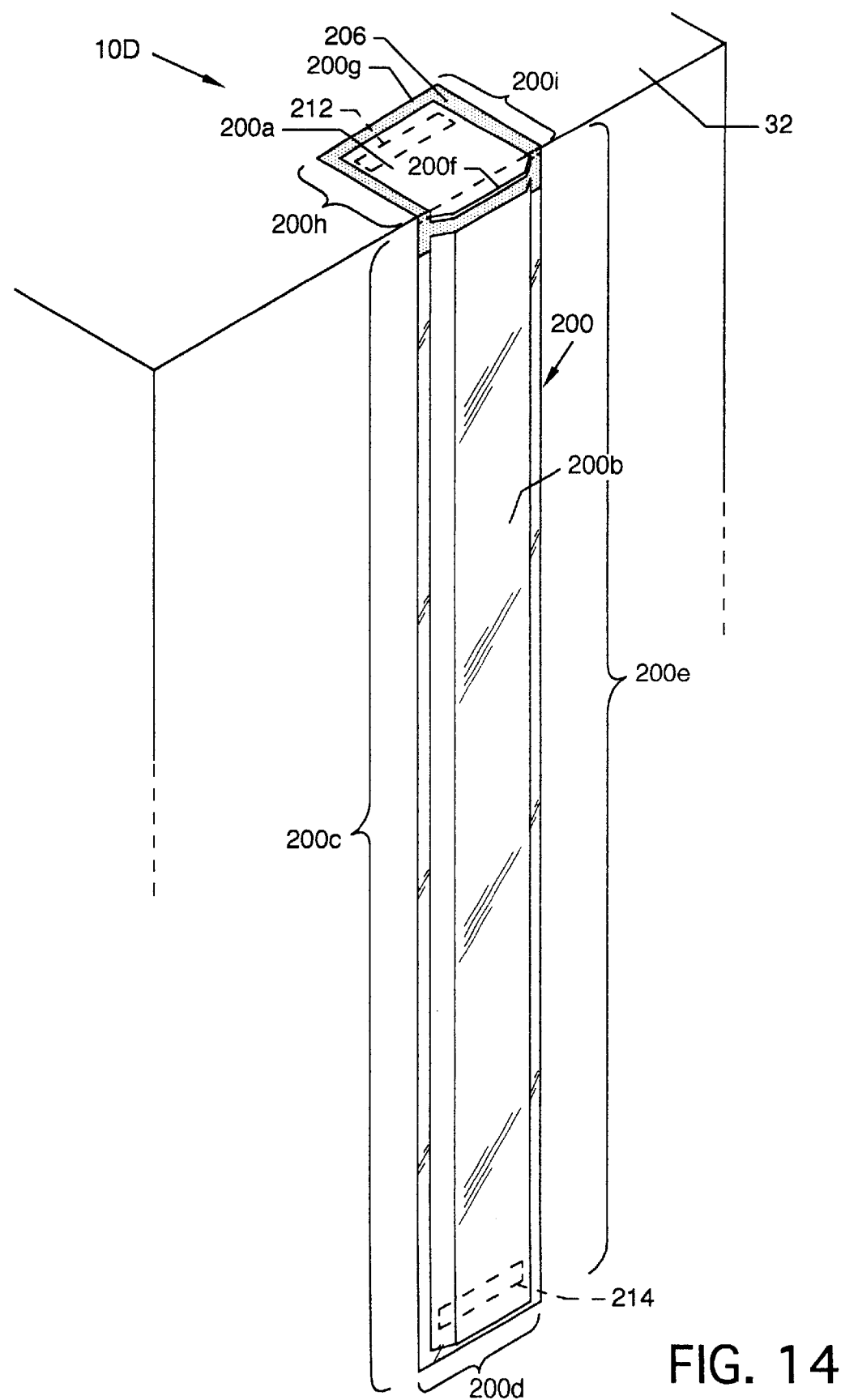
FIG. 14, a fourth alternative embodiment, illustrates an isometric view of a suction catheter in a position for use.
Figure 15:
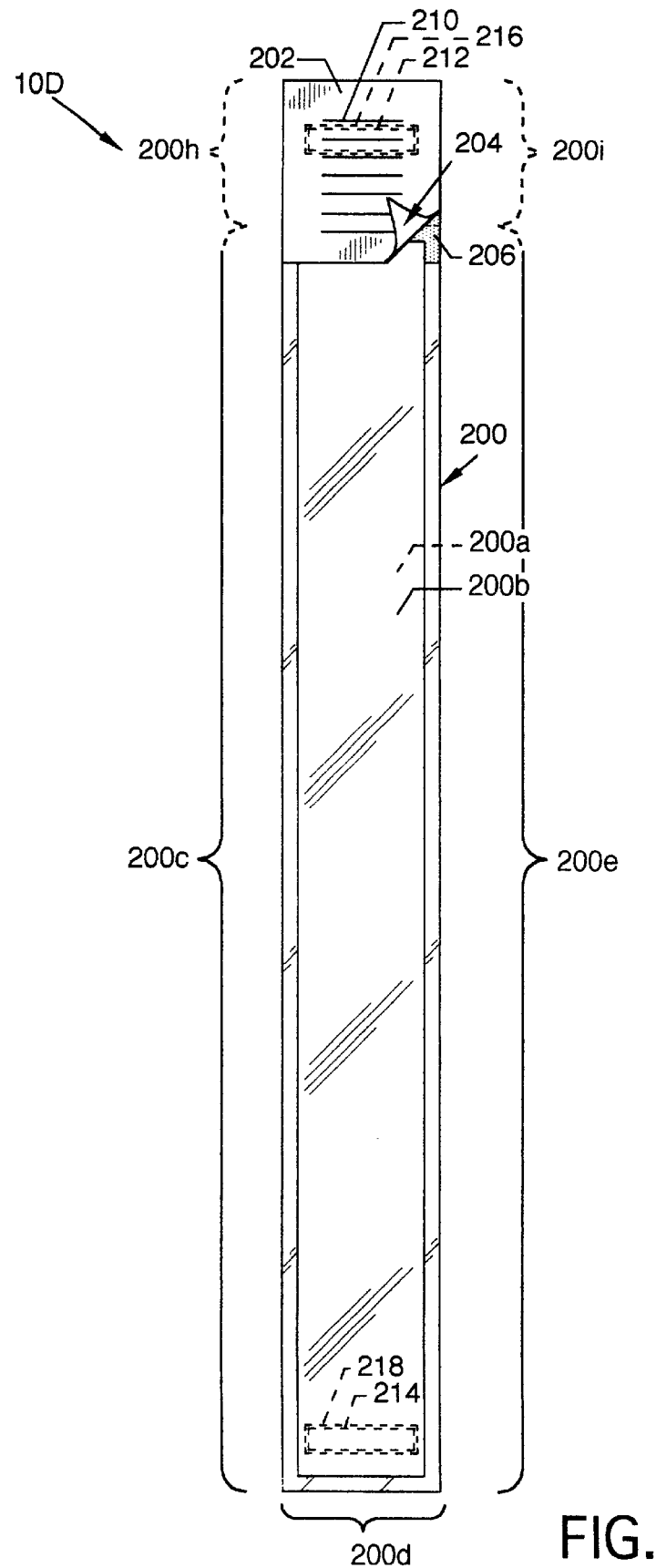
FIG. 15 illustrates a front view of the suction catheter system as it would be packaged before use.
Figure 16:
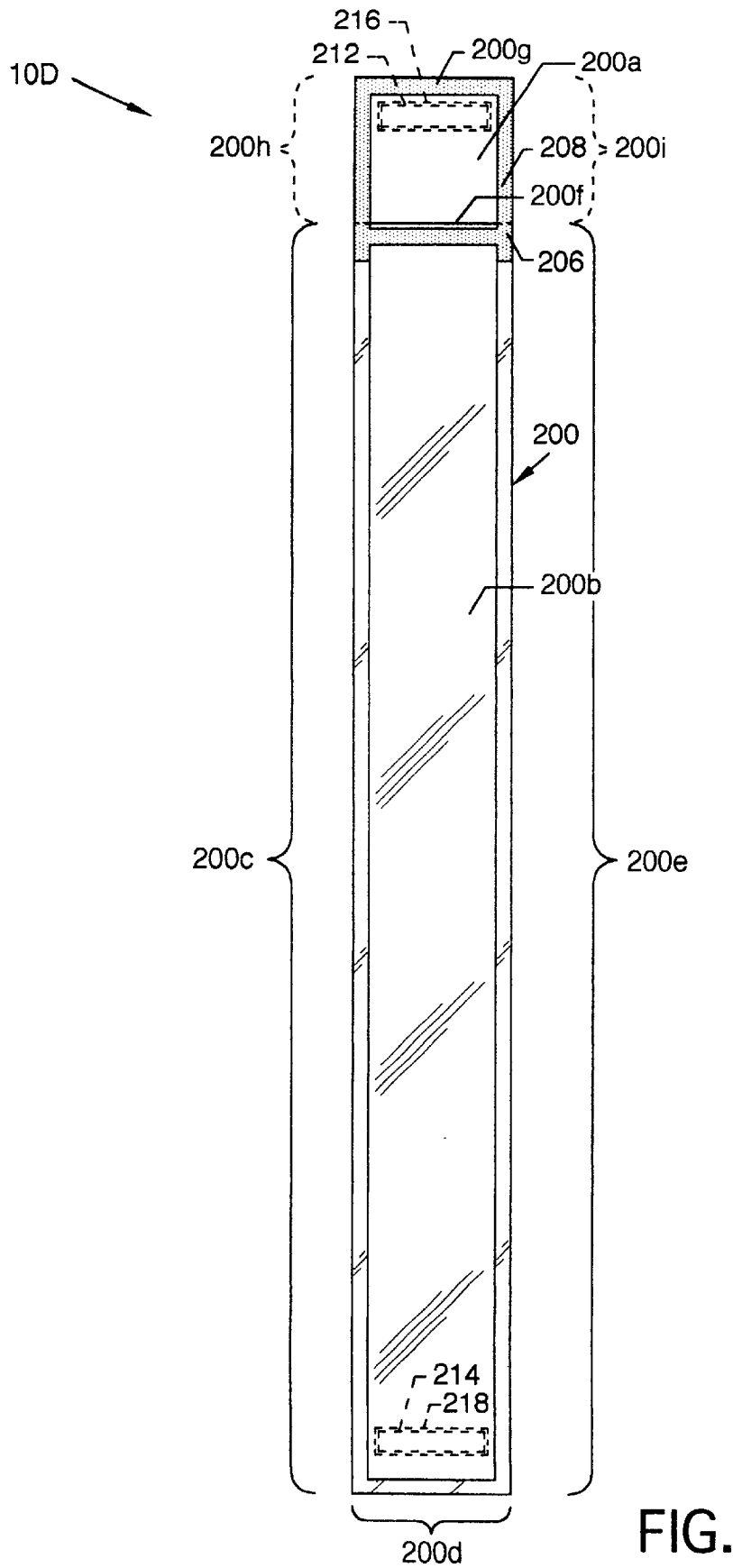
FIG. 16 illustrates a front view of the suction catheter system prior to full utilization.

FIG. 14, a fourth alternative embodiment, illustrates an isometric view of a suction catheter system 10D represented by its most prominent feature, an elongated pouch 200 which, like the pouch 18, is transparent, and which is constructed in accordance with many of the elements and structures described in FIGS. 1–5. The elongated pouch 200 could contain a suction tube but does not include a set of surgical gloves. FIG. 15 illustrates a front view of the suction catheter system 10D as it would be packaged before use; and FIG. 16 illustrates a front view of the suction catheter system 10D with a sealing panel 202 removed. The transparent elongated pouch 200 fashioned generally of durable, clear and transparent flexible plastic panels, includes a rear panel 200*a* which is continuous with an anchoring flap 200*h* of TYVEK® or other suitable material and a front panel 200*b* of durable, clear and transparent flexible plastic material of a shorter vertical dimension than that of the rear panel 200*a*. The shorter front panel 200*b* is suitably secured and bonded to the rear panel 200*a*, such as by ultrasonic welding, heat treatment, adhesive or the like, thereby forming planar connected layered planar edges including a left planar edge 200*c*, a bottom planar edge 200*d*, and a right planar edge 200*e*. The shorter front panel 200*b* can include extra panel material to allow for outward expansion for carriage of a catheter and/or irrigating solution, if desired. Suitably located one-time use medium pressure sensitive adhesive 204 is provided on the rear surface of a sealing panel 202 to enable sealing of the elongated pouch 200 by the sealing panel 202. The one-time use medium pressure sensitive adhesive 204 on the rear surface of the sealing panel 202 seals along a sealing path 206 extending along the top planar edge 200*g* of the rear panel 200*a*, downwardly from the top planar edge 200*g* of the rear panel 200*a* along the left and right planar edges 200*h* and 200*i*, respectively, of the rear panel 200*a* and beyond the upper edge or lip 200*f* of the front panel 200*b* continuing a short distance onto the left planar edge 200*c* and right planar edge 200*e*, and horizontally across the front panel 200*b* between the left planar edge 200*c* and the right planar edge 200*e* in close proximity to the upper edge or lip 200*f* of the front panel 200*b*. In the alternative, one-time use medium pressure sensitive adhesive, shown alternatively with reference numeral 208, could be applied to the sealing path 206 in lieu of the one-time use medium pressure sensitive adhesive 204 on the rear surface of the sealing panel 202. Such adhesive arrangements offer a suitable arrangement for sealing of the elongated pouch 200 by sealing panel 202. In addition, instructions 210 are included on the front surface of the sealing panel 202. The elongated pouch 200 includes one or more double-sided adhesive strips 212 and 214 on the backside of the rear panel 200*a* of the elongated pouch 200 which secures the elongated pouch 200 in an upright fashion to a wall, a bed rail, an IV pole, the side of a cabinet, an operating room table or any other suitable structure at any suitable location. The forward sides of the adhesive strips 212 and 214 adhere to the rearward side of the rear panel 200*a* by high pressure sensitive adhesive (not illustrated) and the rearward side of the adhesive strips 212 and 214 are coated with a medium pressure sensitive adhesive for adhesion to a suitable nearby structure. Backing strips 216 and 218 are located on the rear of the adhesive strips 212 and 214, respectively. All of the strips of adhesive are of a medical grade, non-latex and hypoallergenic material.

Figure 17:
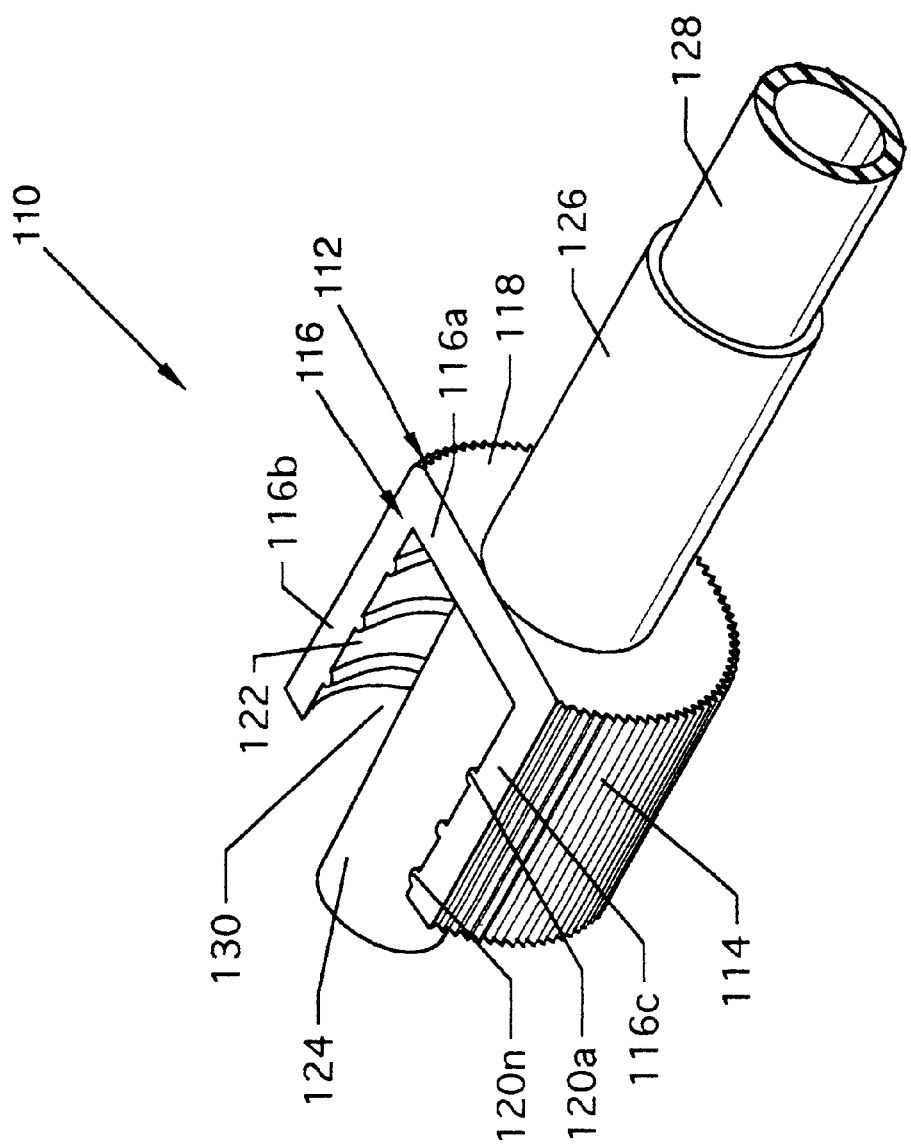
FIG. 17, a fifth alternative embodiment, illustrates an isometric view of a flat-sided Luer lock.

FIG. 17, a fifth alternative embodiment, illustrates an isometric view of a flat-sided Luer lock 110 including a truncated cylindrical body 112. The view presented in FIG. 17 is inverted for purpose of illustration. The wall 114 of the truncated cylindrical body 112 is truncated along a chord of the truncated cylindrical body 112 represented by a planar surface 116*a* extending across the truncated cylindrical body 112, as well as along an edge of a disk-shaped panel 118 which is also truncated. The planar surface 116*a* is contiguous with and aligns with planar surfaces 116*b* and 116*c* of the truncated cylindrical body 112 which collectively comprise a substantially flat U-shaped flat planar surface 116, thus imparting a reduced profile body such as truncated cylindrical body 112. The planar and truncated disk-shaped panel 118 extends downwardly from the edge of the planar surface 116*a* and across one end of the wall 114. Wall 114 is grooved to allow the practitioner to effectively grasp the flat-sided Luer lock 110. A plurality of truncated threads 120*a*–120*n* are located on and extend inwardly from the inner curved surface 122 of the truncated cylindrical body 112. Truncated threads 120*a*-120*n* are located and oriented to mate with a suitably oriented catheter 134 (FIG. 19) so that full and proper engagement of the catheter 134 with the flat-sided Luer lock 110 results in suitable orientation with the U-shaped flat planar surface 116 parallel to the epidermis 146. Initial placement of the catheter 134 requires that the flange 144 (FIG. 19) be suitably oriented whereby the flat test region of the flange 144 is parallel to the epidermis 146. A tapered cylinder 124 extends concentric to and along the centerline of the truncated cylindrical body 112 for subsequent frictional engagement to and with an intravenous catheter. Extending in opposition to the tapered cylinder 124 and from the planar and truncated disk-shaped panel 118 is a cylindrical extension 126 the center of which accommodatingly serves as an attachment fixture for intravenous tubing 128. Tapered cylinder 124 and cylindrical extension 126 include a common passage 132 (FIG. 18) which also extends through the planar and truncated disk-shaped panel 118 for passage of medicinal fluids through the flat-sided Luer lock 110. A space 130 is included between the inner curved surface 122 and the tapered cylinder 124 for accommodation of an intravenous catheter. Alternatively, the truncated cylindrical body 112 and the attributes thereof can be incorporated into use with a slip Luer lock (not illustrated). A slip Luer lock is a Luer lock that can slide back and forth about one-third of an inch toward the end of the intravenous tubing to engage an intravenous catheter.

Figure 18:
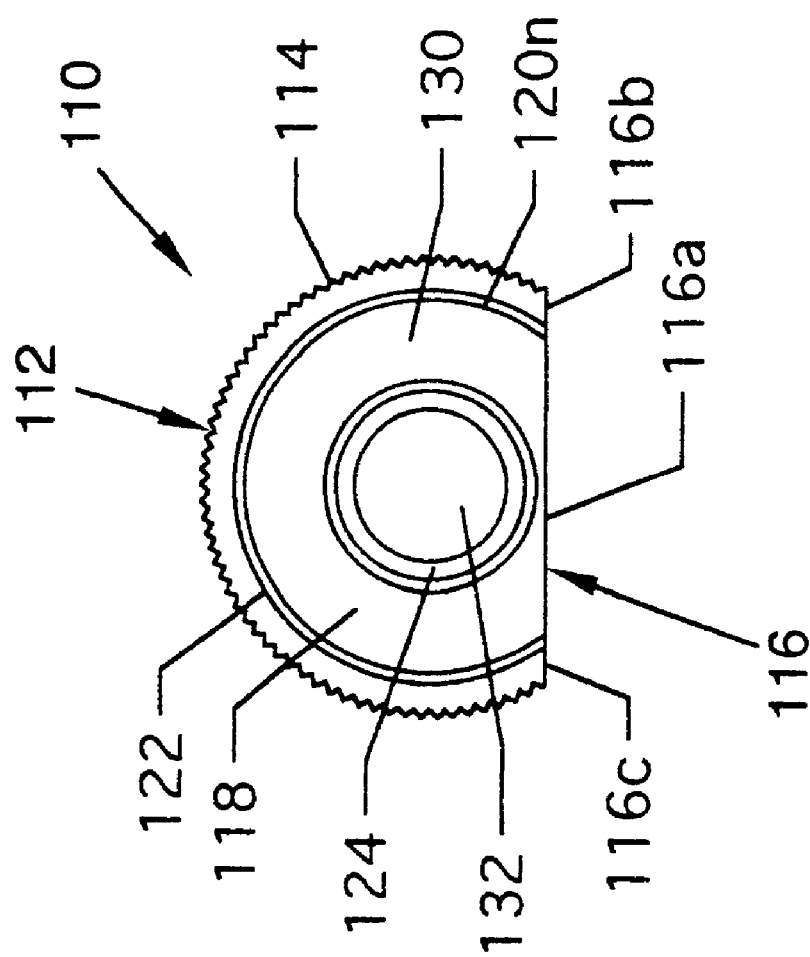
FIG. 18 illustrates an end view of the flat-sided Luer lock.

FIG. 18 illustrates an end view of the flat-sided Luer lock 110, where all numerals correspond to those elements previously described. Illustrated in particular is the common passage 132 passing through the tapered cylinder 124, the planar and truncated disk-shaped panel 118 and the cylindrical extension 126 (not shown).

Figure 19:
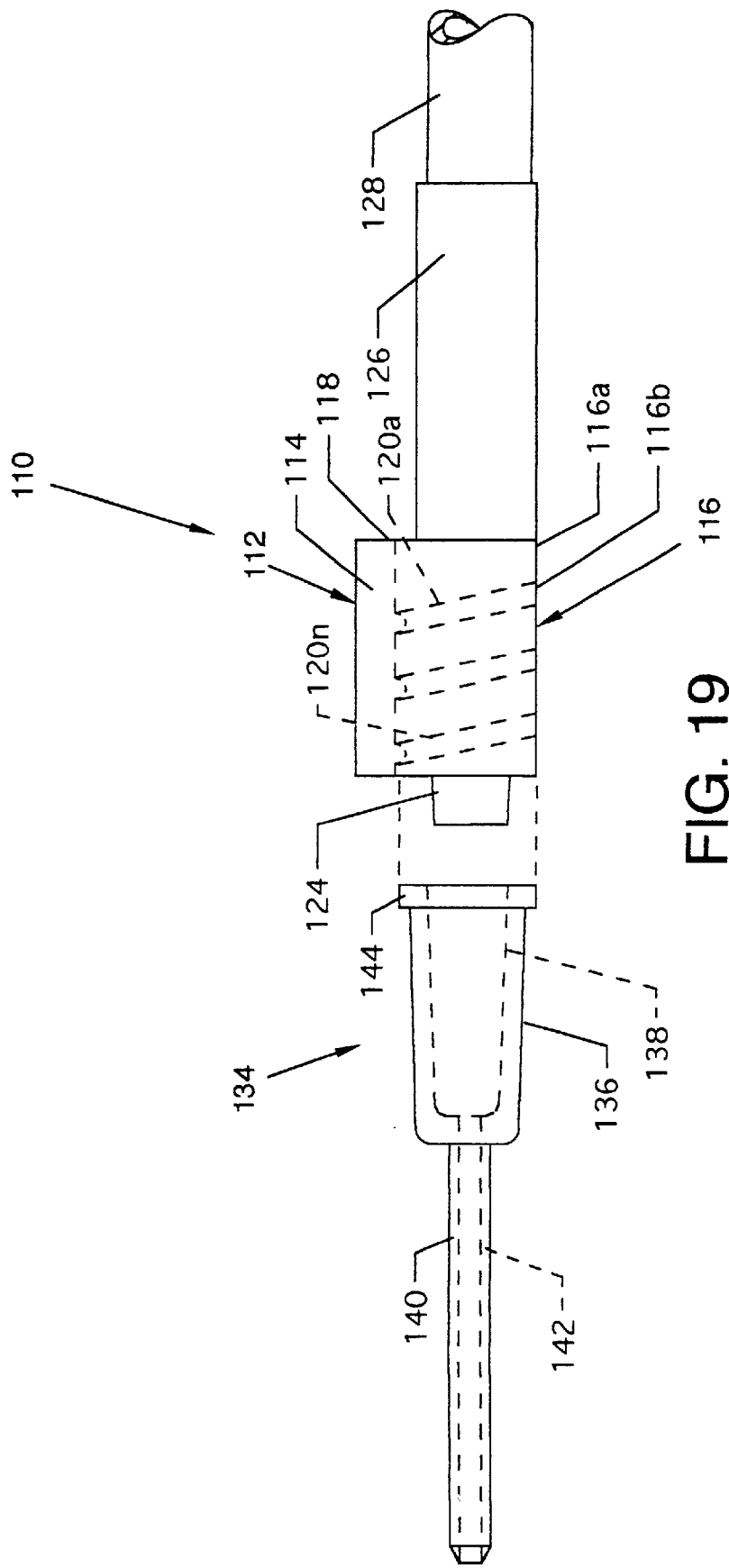
FIG. 19 illustrates a side view of the flat-sided Luer lock and of an intravenous catheter aligned prior to mutual engagement.

FIG. 19 illustrates a side view of the flat-sided Luer lock 110 and of an intravenous catheter 134 aligned prior to engagement with the flat-sided Luer lock 110, where all numerals mentioned previously correspond to those elements previously described. The intravenous catheter 134 includes a tapered body 136 having a tapered interior 138, a slender cylinder 140 extending from the tapered body 136, and a passage 142 in the cylinder 140 connected to the tapered interior 138. A flange 144 is located at one end of the tapered body 136 for engagement with interior truncated threads 120a–120n of the truncated cylindrical body 112. It is noted that the flange 144 does not extend beyond the lower extent of the planar surface 116.

Figure 20:
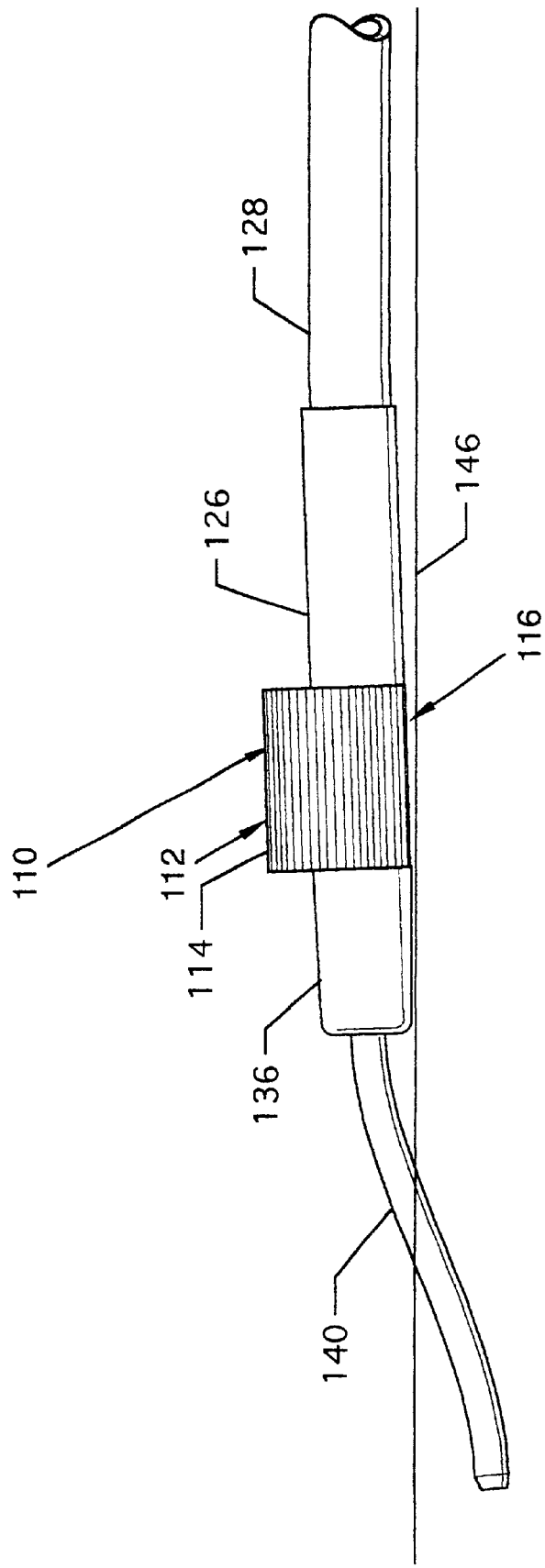
FIG. 20 illustrates the use of the flat-sided Luer lock and catheter.

FIG. 20 illustrates the use of the flat-sided Luer lock 110 with a catheter 134, where all numerals mentioned previously correspond to those elements previously described. Due to the reduced profile of the flat-sided Luer lock 110, impingement of the flat-sided Luer lock 110 with the epidermis 146 is eliminated or minimized, thus reducing or eliminating trauma, irritation and the like at the epidermis 146.

Figure 21:
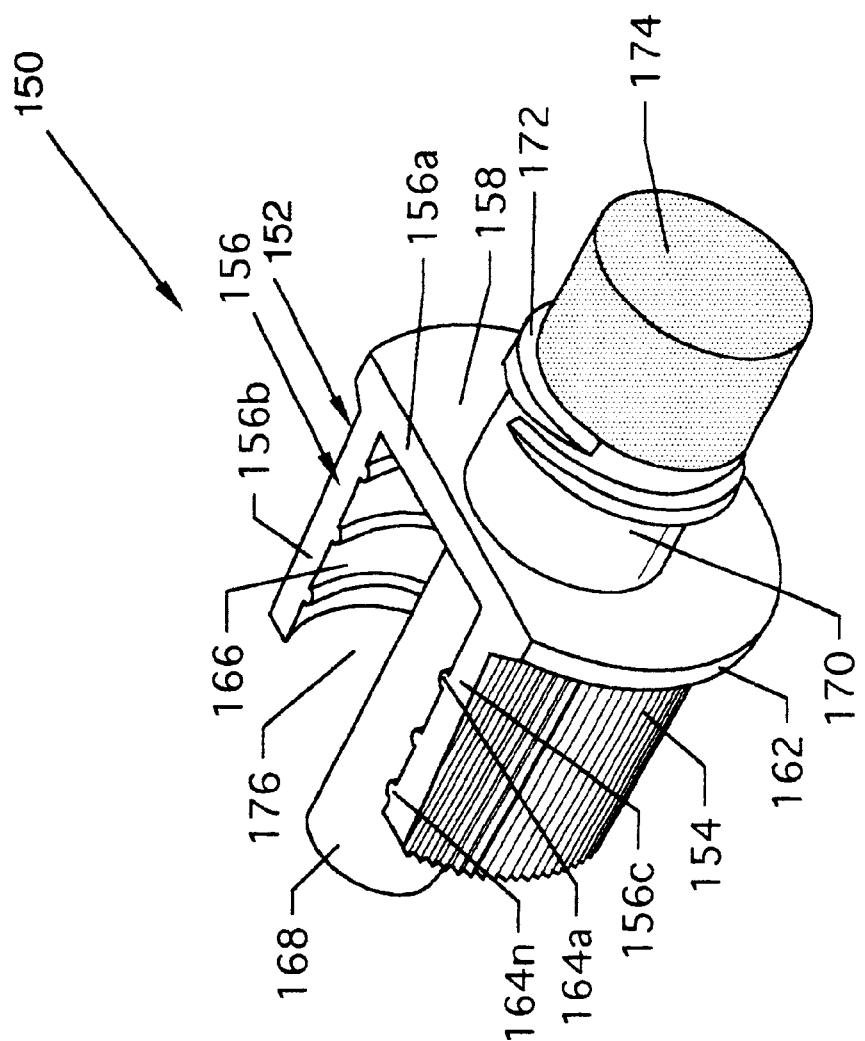
FIG. 21, a sixth alternative embodiment, illustrates an isometric view of a flat-sided Luer lock injection site connector.

FIG. 21, a sixth alternative embodiment, illustrates an isometric view of a flat-sided Luer lock injection site connector 150 including a truncated cylindrical body 152. The view presented in FIG. 21 is inverted for purpose of illustration. The wall 154 of the truncated cylindrical body 152 is truncated along a chord of the truncated cylindrical body 152 represented by a greater portion of the planar surface 156a extending across the truncated cylindrical body 152 and laterally beyond. The planar surface 156a also forms the top of a disk-shaped panel 158 which is also truncated. The disk-shaped and truncated panel 158 extends across one end of the truncated cylindrical body 152. Planar surfaces 156b and 156c located on the truncated cylindrical body 152 are contiguous with and align to the planar surface 156a. Aligned surfaces including planar surface 156a, planar surface 156b and planar surface 156c collectively comprise a substantially flat U-shaped flat planar surface 156, thus imparting a reduced profile body such as truncated cylindrical body 152. It is also noted that the U-shaped flat planar surface 156 in FIG. 21 is angled or canted upwardly, as shown, from the distal portion of the U-shaped flat planar surface 156 to meet the level of raised thread 172. Such an arrangement ensures that the profile of the raised thread 172 does not extend beyond the general profile of the flat-sided Luer lock injection site connector 150, thus preventing the raised thread 172 from depressed contact with the epidermis. The truncated disk-shaped panel 158 of a larger radius than the truncated cylindrical wall 154 extends across and along one end of the wall 154 to form a lip 162. A plurality of truncated threads 164a–164n are located on and extend inwardly from the inner curved surface 166 of the truncated cylindrical body 152. As with the truncated threads 120a–120n of the flat-sided Luer lock 110, truncated threads 164a–164n of the flat-sided Luer lock injection site connector 150 are located and oriented to mate with a suitably oriented catheter, such as catheter 134 or catheter 180 (FIG. 23) so that full and proper engagement of the catheter 180 with the flat-sided Luer lock injection site connector 150 results in suitable orientation with the U-shaped flat planar surface 156 parallel to the epidermis 146. Placement of the catheter 180 requires that flange 190 (FIG. 23) be suitably oriented where that flatest region of the flange 190 is parallel to the epidermis 140 and that the largest span of the flange 190 is parallel to the epidermis so that no part of the flange 190 extends below the U-shaped flat planar surface 156. Proper orientation of the threads 120a–120n of the flat-sided Luer lock 110 and the threads 164a–164n of the flat-sided Luer lock injection site connector 150 is desirable in that either the flat-sided Luer lock 110 or the flat-sided Luer lock injection site connector 150 can be suitably oriented, interchanged and attached to catheter such as catheters 134 and 180. The threads 120a–120n of the flat-sided Luer lock 110 and the threads 164a–164n of the flat-sided Luer lock injection site connector 150 can be properly constructed and oriented during the manufacturing process to ensure proper orientation of flanges 144 and 190 so that when fully engaged, the widest portion of the flanges 144 and 190 are in close engagement with the threads and so that no profile of the flanges 144 and 190 extend below the flat surfaces 116 or 156. A tapered cylinder 168 extends concentric to and along the centerline of the truncated body 152 for subsequent frictional engagement to and with an intravenous catheter. Extending in opposition to the tapered cylinder 168 and from the truncated disk-shaped panel 158 is a cylindrical extension 170 having a raised thread 172 located along the cylindrical extension 170 and a puncturable self-sealing membrane 174 fitted over and about the portion of the cylindrical extension 170 outboard of the raised thread 172 and covering the proximal end of the cylindrical extension 170. The raised thread 172 can function as a stop for attached membrane puncturing members or can serve to attach an intravenous fitting which can align over and about the membrane 174 while at the same time puncturing the membrane 174. Alternatively, an annular ring without a thread can be incorporated in lieu of the raised thread 172. Tapered cylinder 168 and cylindrical extension 170 include a common passage 178 (FIG. 22) which also extends through the truncated disk-shaped panel 158 for passage of medicinal fluids through the flat-sided Luer lock injection site connector 150. A space 176 is included between the inner curved surface 166 and the tapered cylinder 168 for accommodation of an intravenous catheter. Wall 154 is grooved to allow the practitioner to effectively grasp the flat-sided Luer lock injection site connector 150.

Figure 22:
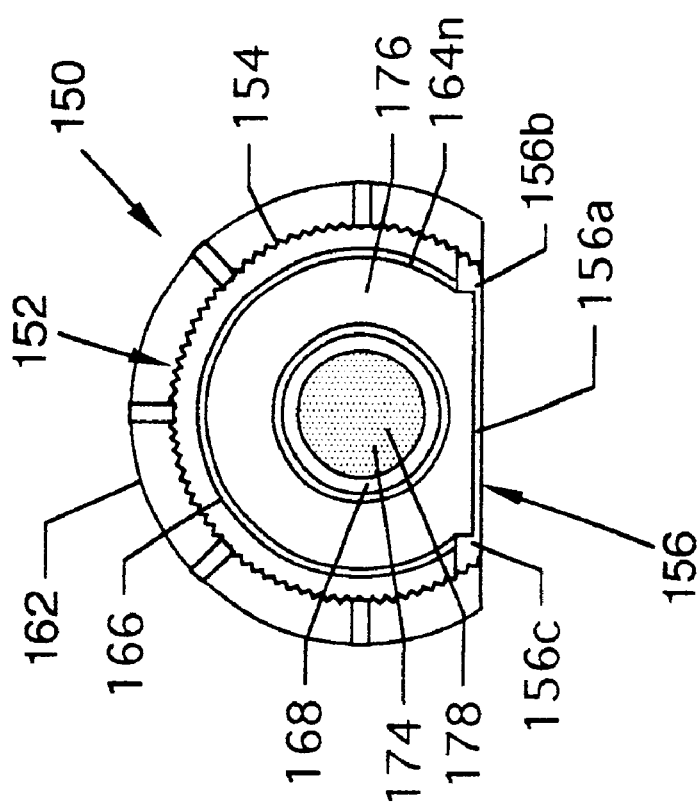
FIG. 22 illustrates an end view of the flat-sided Luer lock injection site connector.

FIG. 22 illustrates an end view of the flat-sided Luer lock injection site connector 150, where all numerals correspond to those elements previously described. Illustrated in particular is the common passage 178 passing through the tapered cylinder 168, the truncated disk-shaped panel 158 and the cylindrical extension 170 (not shown).

Figure 23:
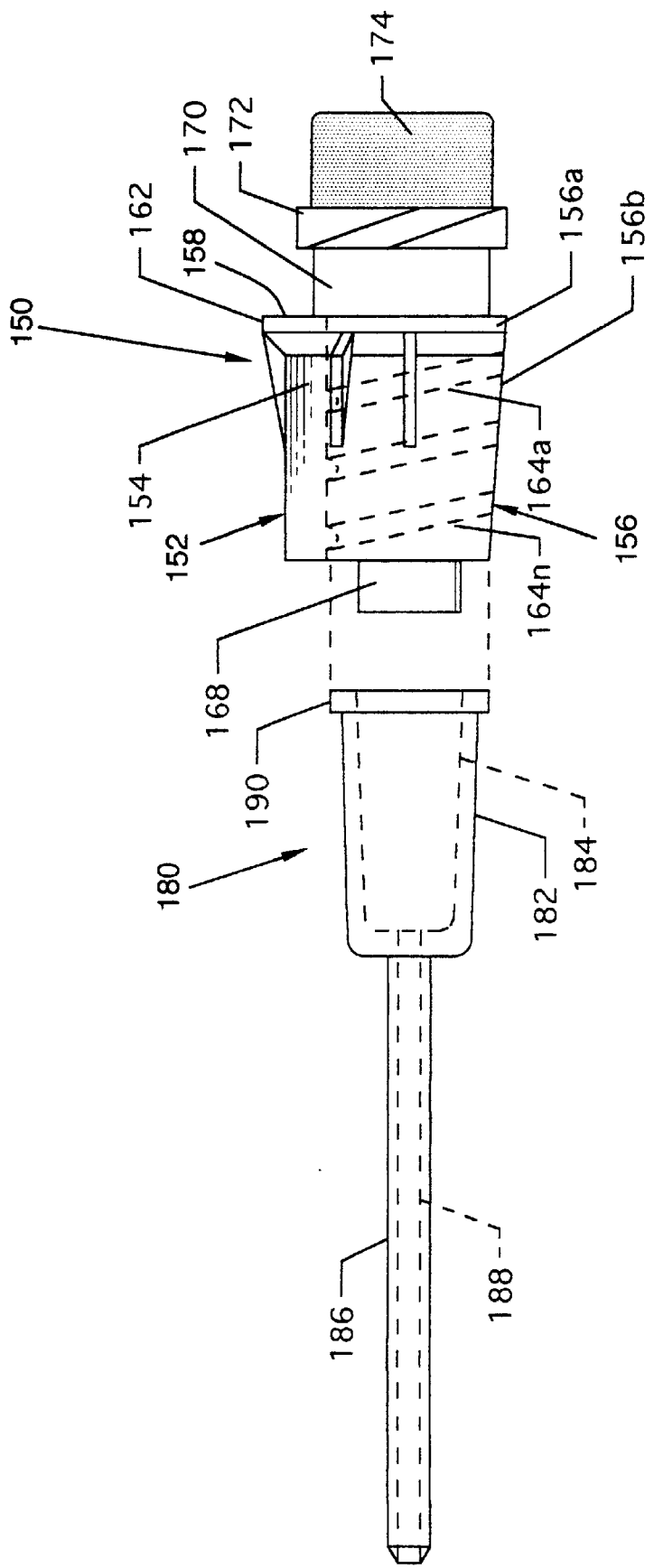
FIG. 23 illustrates a side view of the flat-sided Luer lock injection site connector and of an intravenous catheter aligned prior to mutual engagement; and, FIG. 24 illustrates the use of the flat-sided Luer lock injection site connector and catheter.

FIG. 23 illustrates a side view of the flat-sided Luer lock injection site connector 150 and of an intravenous catheter 180 aligned prior to engagement with the flat-sided Luer lock injection site connector 150, where all numerals mentioned previously correspond to those elements previously described. The intravenous catheter 180 includes a tapered body 182 having a tapered interior 184, a slender cylinder 186 extending from the tapered body 182, and a passage 188 in the cylinder 186 connected to the tapered interior 184. A flange 190 is located at one end of the tapered body 182 for engagement with interior truncated threads 164a–164n of the truncated cylindrical body 152. It is noted that the flange 190 does not extend beyond the lower extent of the planar surface 156.

Figure 24:
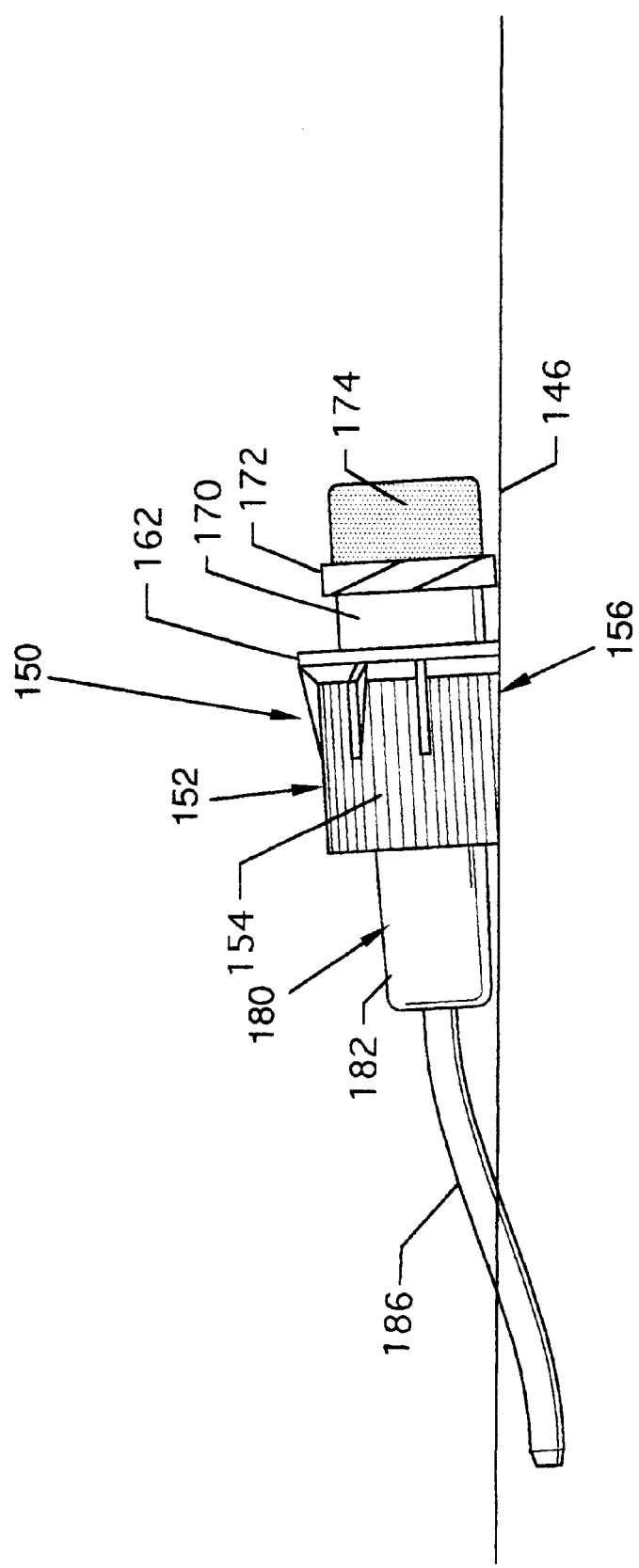

FIG. 24 illustrates the use of the flat-sided Luer lock injection site connector 150 with a catheter 180. Due to the reduced profile of the flat-sided Luer lock injection site connector 150, impingement of the flat-sided Luer lock injection site connector 150 with the epidermis 146 is eliminated or minimized, thus reducing or eliminating trauma, irritation and the like at the epidermis 146.

Various modifications can be made to the present invention without departing from the apparent scope hereof.

| | |
|---|---|
| 10 | suction catheter system |
| 10A | suction catheter system |
| 10B | suction catheter system |
| 10C | suction catheter system |
| 12 | catheter |
| 14 | catheter tip |
| 16 | catheter stem |
| 18 | pouch |
| 18a | rear panel |
| 18b | front panel |
| 18c | left planar edge |
| 18d | bottom planar edge |
| 18e | right planar edge |
| 18f | upper edge or lip |
| 18g | top planar edge |
| 18h | left planar edge |
| 18i | right planar edge |
| 18j | anchoring flap |
| 20 | irrigating solution |
| 22 | pull tab |
| 24 | double-sided adhesive strip |
| 26 | double-sided adhesive strip |
| 28 | double-sided adhesive strip |
| 32 | work surface |
| 34 | surgical gloves |
| 35 | sealing panel |
| 35a | sealing panel |
| 36 | instructions |
| 39 | sterile wrapping |
| 40 | backing strip |
| 42 | backing strip |
| 44 | backing strip |
| 46 | one-time use medium pressure sensitive adhesive |
| 47 | sealing path |
| 48 | one-time use medium pressure sensitive adhesive |
| 50 | pull tab |
| 60 | elongated pouch |
| 60a | rear panel |
| 60b | front panel |
| 60c | flap |
| 60d | upper edge or lip |
| 60e | left planar edge |
| 60f | bottom planar edge |
| 60g | right planar edge |
| 60h | anchoring flap |
| 60i | corner |
| 60j | corner |
| 61 | high pressure sensitive double-sided adhesive strip |
| 62 | one-time use medium pressure sensitive adhesive |
| 63 | high pressure sensitive adhesive |
| 64 | sealing path |
| 66 | one-time use medium pressure sensitive adhesive |
| 68 | double-sided adhesive strip |
| 70 | double-sided adhesive strip |
| 74 | backing strip |
| 76 | backing strip |
| 77 | line |
| 84 | transparent pouch |
| 84a | rear panel |
| 84b | front panel |
| 84c | flap |
| 84d | upper edge or lip |
| 84e | left planar edge |
| 84f | bottom planar edge |
| 84g | right planar edge |
| 84h | anchoring flap |
| 84i | corner |
| 84j | corner |
| 86 | high pressure sensitive double-sided adhesive strip |
| 88 | high pressure sensitive double-sided adhesive strip |
| 90 | flexible compartment |
| 92 | line |
| 94 | one-time use medium pressure sensitive adhesive |
| 96 | one-time use medium pressure sensitive adhesive |
| 98 | sealing path |
| 100 | high pressure sensitive adhesive |
| 102 | double-sided adhesive strip |
| 104 | backing strip |
| 106 | arrow |
| 108 | arrow |
| 110 | flat-sided Luer lock |
| 112 | truncated cylindrical body |
| 114 | wall |
| 116 | U-shaped flat planar surface |
| 116a–c | planar surfaces |
| 118 | planar and truncated disk-shaped panel |
| 120a–n | truncated threads |
| 122 | inner curved surface |
| 124 | tapered cylinder |
| 126 | cylindrical extension |
| 128 | intravenous tube |
| 130 | space |
| 132 | common passage |
| 134 | catheter |
| 136 | tapered body |
| 138 | tapered interior |
| 140 | cylinder |
| 142 | passage |
| 144 | flange |
| 146 | epidermis |
| 150 | flat-sided Luer lock injection site connector |
| 152 | truncated cylindrical body |
| 154 | wall |
| 156 | U-shaped flat planar surface |
| 156a–c | planar surfaces |
| 158 | truncated disk-shaped panel |
| 162 | lip |
| 164a–n | truncated threads |

-continued

| | |
|---|---|
| 166 | inner curved surface |
| 168 | tapered cylinder |
| 170 | cylindrical extension |
| 172 | raised thread |
| 174 | membrane |
| 176 | space |
| 178 | common passage |
| 180 | catheter |
| 182 | tapered body |
| 184 | tapered interior |
| 186 | cylinder |
| 188 | passage |
| 190 | flange |
| 200 | elongated pouch |
| 200a | rear panel |
| 200b | front panel |
| 200c | left planar edge |
| 200d | bottom planar edge |
| 200e | right planar edge |
| 200f | upper edge or lip |
| 200g | top planar edge |
| 200h | anchoring flap |
| 202 | sealing panel |
| 204 | one-time use medium pressure sensitive adhesive |
| 206 | sealing path |
| 208 | one-time use medium pressure sensitive adhesive |
| 210 | instructions |
| 212 | double-sided adhesive strip |
| 214 | double-sided adhesive strip |
| 216 | backing strip |
| 218 | backing strip |

What is claimed is:

1. A suction catheter system kit comprising:
  a. a pouch, the pouch having a front panel and a rear panel, the rear panel bonded to the front panel at a bottom edge, a right edge, and a left edge and extending past the front panel at a fold to form an anchoring flap, the anchoring flap sealing the pouch by a one-time seal to the front panel along a sealing path, such that a front surface of the rear panel is disposed adjacent a front surface of the front panel, thereby defining a sealed volume within the pouch;
  b. a suction catheter within the sealed volume of the pouch, the suction catheter having a catheter tip and a catheter stem; and,
  c. work surface attachment means on the anchoring flap.

2. The suction catheter system kit of claim 1, further comprising a pair of sterile surgical gloves within the sealed volume of the pouch.

3. The suction catheter system kit of claim 2, wherein the sterile surgical gloves are surrounded by a sterile wrapping.

4. The suction catheter system kit of claim 1, further comprising instructions, the instructions being associated with the kit.

5. The suction catheter system kit of claim 4, wherein the instructions are printed on the pouch.

6. The suction catheter system kit of claim 5, wherein the instructions are printed on the flap.

7. The suction catheter system kit of claim 6, wherein the instructions are printed on the front side of the flap and oriented for reading such that the instructions may be read by a practitioner situated in front of the pouch when the sealing path has been opened and the pouch is being supported by the work surface attachment means on the anchoring flap.

8. The suction catheter system kit of claim 7, wherein the pouch is transparent so as to allow the instructions to be read prior to unsealing the kit.

9. The suction catheter system kit of claim 1, wherein the pouch is transparent.

10. The suction catheter system kit of claim 1, wherein the attachment means included a double-sided adhesive strip covered by a backing strip on a backside of the anchoring flap.

11. The suction catheter system kit of claim 10, wherein the double-sided adhesive and the anchoring flap, subsequent to opening the sealing path and folding the anchoring flap, can support the pouch from a work surface when the fold is situated at an edge of the work surface and a reservoir of irrigating liquid is placed in the pouch.

12. The suction catheter system kit of claim 1, wherein the sealed volume within the pouch is sterile.

13. The suction catheter system kit of claim 1, wherein the sealed volume within the pouch and the catheter are sterile.

14. A suction catheter system comprising:
  a. a pouch, the pouch having a front panel and a rear panel, the rear panel bonded to the front panel at a bottom edge, a right edge, and a left edge and extending past the front panel at a fold to form an anchoring flap, the anchoring flap initially sealing the pouch by a one-time seal to the front panel along a sealing path, such that a front surface of the rear panel is disposed adjacent a front surface of the front panel, thereby defining a sealed volume within the pouch;
  b. a suction catheter within the sealed volume of the pouch; and,
  c. work surface attachment means on the anchoring flap;
  d. wherein the sealing path may be disrupted to remove the suction catheter and the pouch may be subsequently supported by the anchoring flap to serve as a container for a reservoir of irrigating liquid.

15. The suction catheter system of claim 14, further comprising a pair of sterile surgical gloves initially contained within the sealed volume of the pouch.

16. The suction catheter system kit of claim 15, wherein the sterile surgical gloves are surrounded by a sterile wrapping.

17. The suction catheter system of claim 14, further comprising instructions, the instructions being associated with the kit.

18. The suction catheter system of claim 17, wherein the instructions are printed on the pouch.

19. The suction catheter system of claim 18, wherein the instructions are printed on the flap.

20. The suction catheter system of claim 19, wherein the instructions are printed on the front side of the flap and oriented for reading such that the instructions may be read by a practitioner situated in front of the pouch when the pouch is opened and being supported by the work surface attachment means on the anchoring flap.

21. The suction catheter system of claim 14, wherein the pouch is transparent.

22. The suction catheter system of claim 21, wherein the pouch is transparent so as to allow the instructions to be read prior to unsealing the sealing path.

23. The suction catheter system of claim 14, wherein the attachment means included a double-sided adhesive strip covered by a backing strip on a backside of the anchoring flap.

24. The suction catheter system of claim 23, wherein the double-sided adhesive and the anchoring flap, subsequent to opening the sealing path and folding the anchoring flap, can support the pouch from a work surface when the fold is situated at an edge of the work surface and a reservoir of irrigating liquid is placed in the pouch.

25. The suction catheter system of claim 24, wherein the sealed volume within the pouch is initially sterile.

26. The suction catheter system of claim 14, wherein the sealed volume within the pouch and the catheter are sterile.

27. A process for using a suction catheter comprising the steps of:
   a. providing a sealed pouch, the pouch having a front panel and a rear panel, the rear panel and the front panel being bonded at a bottom edge, a right edge and a left edge, and the rear panel having a flap with a one-time sealing path to the front panel, thereby defining a initially sealed volume, and having a catheter within the sealed volume;
   b. opening the one-time sealing path;
   c. attaching the flap of the pouch to a horizontal work surface, such that the pouch is depending from the flap;
   d. filling a desired portion of the depending pouch with irrigation solution;
   e. attaching the suction catheter to a suction tubing and suction patient; and,
   f. irrigating the catheter with irrigation solution from the depending pouch.

28. The process of claim 27, wherein the flap carries a double-sided adhesive and a backing strip covering the double-sided adhesive, and the step of attaching the flap of the pouch to a horizontal work surface includes to steps of:
   a. removing the backing strip to expose the double-sided adhesive; and,
   b. contacting the exposed doubled-sided adhesive with the horizontal work surface.

29. The process of claim 27, wherein the sealed volume of the pouch further includes a pair of sterile surgical gloves, and the method further includes the steps of:
   a. removing the surgical gloves; and,
   b. donning the surgical gloves.

30. The process of claim 29, wherein the pair of sterile surgical gloves are initially within a sterile wrap, and the step of removing the surgical gloves includes the step of dropping the surgical gloves, within the sterile wrap, from the pouch.

31. The process of claim 30, wherein the sterile wrap is retained for subsequent manipulation, using a remaining sterile surface of the sterile wrap.

32. The process of claim 27, wherein the process further includes the step of replacing a portion of the catheter in the pouch to avoid contamination.

33. The process of claim 32, wherein the suction catheter further includes an adhesive strip on the stem of the suction catheter to temporarily secure the suction catheter to the pouch when replacing a portion of the catheter in the pouch.

34. The process of claim 33, further comprising the step of squeezing the outside of the pouch to force contact between the adhesive strip on the stem of the suction catheter and the inside of the pouch.

35. The process of claim 32, wherein the pouch further includes an adhesive strip situated to temporarily secure the stem of the suction catheter to the pouch when replacing a portion of the catheter in the pouch.

36. The process of claim 39, further comprising the step of squeezing the outside of the pouch to force contact between the adhesive strip situated to temporarily secure the stem of the suction catheter and the stem of the suction catheter.

37. The process of claim 27, wherein the pouch is sized to require the catheter to be folded to fit within the pouch.

38. The process of claim 27, wherein the pouch is sized to allow the catheter to be extended to fit within the pouch.

39. The process of claim 38, wherein the pouch has elongated right and left edges relative to the anchoring flap and bottom end, such that when the pouch depends from the anchoring flap, the reservoir of irrigation solution is vertically oriented.

40. The process of claim 39, wherein the elongated pouch has a lower adhesive strip adjacent the bottom edge to additionally secure the pouch to a vertical surface while depending from the horizontal work surface.

41. The process of claim 27, wherein the flap includes a pull tab and the method further includes the step of pulling on the pull tab to open the pouch.

* * * * *